US009216992B2

(12) United States Patent
Ford et al.

(10) Patent No.: US 9,216,992 B2
(45) Date of Patent: *Dec. 22, 2015

(54) THIENO[3,2-C]PYRIDINE POTASSIUM CHANNEL INHIBITORS

(75) Inventors: John Ford, Huntingdon (GB); David John Madge, Cambridgeshire (GB); Helen Jane Payne, Cambridgeshire (GB); Jamie David Knight, Middlesex (GB)

(73) Assignee: Xention Limited, Pampisford, Cambridge (GB)

( * ) Notice: Subject to any disclaimer, the term of this patent is extended or adjusted under 35 U.S.C. 154(b) by 1125 days.

This patent is subject to a terminal disclaimer.

(21) Appl. No.: 11/635,786

(22) Filed: Dec. 8, 2006

(65) Prior Publication Data

US 2007/0161672 A1    Jul. 12, 2007

Related U.S. Application Data

(60) Provisional application No. 60/748,583, filed on Dec. 6, 2005.

(51) Int. Cl.
C07D 495/04 (2006.01)
A61K 31/4365 (2006.01)

(52) U.S. Cl.
CPC ..................... C07D 495/04 (2013.01)

(58) Field of Classification Search
CPC ..................................................... C07D 495/04
See application file for complete search history.

(56) References Cited

U.S. PATENT DOCUMENTS

| 3,845,065 | A | * | 10/1974 | Shen ............................... 46/114 |
| 3,903,095 | A | | 9/1975 | Shen et al. |
| 4,146,716 | A | | 3/1979 | Cox et al. |
| 4,165,374 | A | | 8/1979 | Troxler et al. |
| 6,184,221 | B1 | | 2/2001 | Gerlach et al. |
| 6,521,618 | B2 | * | 2/2003 | Boschelli et al. ........ 514/231.5 |
| 6,531,495 | B1 | | 3/2003 | Brendel et al. |
| 7,199,119 | B2 | * | 4/2007 | Burkitt et al. .............. 514/233.8 |
| 7,456,187 | B2 | | 11/2008 | Ford et al. |
| 7,576,212 | B2 | | 8/2009 | Ford et al. |
| 8,022,076 | B2 | | 9/2011 | Ford et al. |
| 8,193,215 | B2 | | 6/2012 | Ford et al. |
| 2002/0161011 | A1 | | 10/2002 | Beaudoin et al. |
| 2003/0027829 | A1 | | 2/2003 | Reed et al. |
| 2004/0097485 | A1 | | 5/2004 | Burkitt et al. |
| 2004/0180873 | A1 | | 9/2004 | Hanssen et al. |
| 2005/0026935 | A1 | | 2/2005 | Ford et al. |
| 2005/0282829 | A1 | | 12/2005 | Ford et al. |
| 2006/0183768 | A1 | | 8/2006 | Ford et al. |

FOREIGN PATENT DOCUMENTS

| AU | 521790 | 11/1979 |
| DE | 19 65 710 | 7/1970 |
| DE | 28 31 677 A1 | 2/1979 |
| DE | 226 893 A1 | 9/1985 |
| DE | 248 593 A1 | 8/1987 |
| DE | 101 04 802 A1 | 8/2002 |
| EP | 0 126 970 A2 | 12/1984 |
| GB | 1284930 | 8/1972 |
| GB | 1 570 494 | 7/1980 |
| JP | 48-81892 | 11/1973 |
| JP | 48-81893 | 11/1973 |
| JP | 3254843 | 2/1995 |
| JP | 07-076586 | 3/1995 |
| RU | 2 116 309 C1 | 7/1998 |
| WO | WO 98/04521 A1 | 2/1998 |
| WO | WO 98/04542 A1 | 2/1998 |
| WO | WO 98/18475 A1 | 5/1998 |
| WO | WO 98/18476 A1 | 5/1998 |
| WO | WO 99/37607 A1 | 7/1999 |
| WO | WO 99/62891 A1 | 12/1999 |
| WO | WO 00/12492 A1 | 3/2000 |
| WO | WO 00/25774 A1 | 5/2000 |
| WO | WO 01/00573 A1 | 1/2001 |
| WO | WO 01/21609 A1 | 3/2001 |
| WO | WO 01/21610 A1 | 3/2001 |
| WO | WO 01/25189 A1 | 4/2001 |
| WO | WO 01/25224 A1 | 4/2001 |
| WO | WO 01/40231 A1 | 6/2001 |
| WO | WO 01/46155 A1 | 6/2001 |
| WO | WO 02/24655 A1 | 3/2002 |
| WO | WO 01/27107 A2 | 4/2002 |

(Continued)

OTHER PUBLICATIONS

Feit et. al. "Aminobenzoic Acid Diuretics. 8.2 3,4-Disubstituted 5-Methylsulfonylbenzoic Acids and Related Compounds" Journal of Medicinal Chemistry, 1976, 19, 402-406.*
Patani et. al. "Bioisosterism: A Rational Approach in Drug Design" Chemical Reviews 1996, 96, 3147-3176.*
Amos, G.J., et al., "Differences between outward currents of human atrial and subepicardial ventricular myocytes," *J. Physiol.* 491:31-50, Cambridge Univ. Press. (1996).
Armstrong, C.M. and Hille, B., "Voltage-Gated Ion Channels and Electrical Excitability," *Neuron* 20:371-380, Cell Press (1998).
Bachmann, A., et al., "Characterization of a novel Kv1.5 channel blocker in Xenopus oocytes, CHO cells, human and rat cardiomyocytes," *Naunyn-Schmiedeberg's Arch. Pharmacol.* 364:472-478, Springer-Verlag (2001).

(Continued)

*Primary Examiner* — David K O Dell
(74) *Attorney, Agent, or Firm* — Sterne, Kessler, Goldstein & Fox P.L.L.C.

(57) ABSTRACT

The present invention provides thienopyridine compounds which are potassium channel inhibitors. In another embodiment, the invention provides pharmaceutical compositions comprising thienopyridines. In another embodiment, the invention provides methods of using thienopyridines in the treatment or prevention of cancer, arrhythmias, autoimmune diseases and inflammatory diseases, including gastric cancer, atrial fibrillation, type-2 diabetes mellitus, rheumatoid arthritis, type-1 diabetes, inflammatory bowel disorder and demyelinating disorders such as multiple sclerosis.

11 Claims, No Drawings

(56) References Cited

FOREIGN PATENT DOCUMENTS

| WO | WO 02/36556 A2 | 5/2002 |
|---|---|---|
| WO | WO 02/44137 A1 | 6/2002 |
| WO | WO 02/46162 A1 | 6/2002 |
| WO | WO 02/48131 A1 | 6/2002 |
| WO | WO 02/060874 A1 | 8/2002 |
| WO | WO 02/064581 A1 | 8/2002 |
| WO | WO 02/087568 A1 | 11/2002 |
| WO | WO 02/088073 A1 | 11/2002 |
| WO | WO 02/100825 A2 | 12/2002 |
| WO | WO 03/000675 A1 | 1/2003 |
| WO | WO 03/063797 A2 | 8/2003 |
| WO | WO 2004/092123 A2 | 10/2004 |
| WO | WO 2004/111057 A1 | 12/2004 |
| WO | WO 2005/105809 A1 | 11/2005 |
| WO | WO 2006061642 A1 * | 6/2006 |
| WO | WO 2006/106326 A1 | 10/2006 |
| WO | WO 2007005534 A2 * | 1/2007 |

OTHER PUBLICATIONS

Belen'kii, L.I., et al., "Synthesis of Heterocyclic Compounds from the Products of Addition of Polyhaloalkanes to Unsaturated Systems. 4. Synthesis of Substituted Furo[2,3-D]Pyrimidines," *Chemistry of Heterocyclic Compounds* 29:109-114, Plenum Publishing Corporation (1993).

Brendel, J. and Peukert, S., "Blockers of the Kv1.5 channel for the treatment of atrial arrhythmias," *Expert Opin. Ther. Patents* 12:1589-1598, Ashley Publications Ltd. (2002).

Campaigne, E., "Thiophenes and their Benzo Derivatives: (iii) Synthesis and Applications," in *Comprehensive Heterocyclic Chemistry: The Structure, Reactions, Synthesis and Uses of Heterocyclic Compounds* 4, Bird, C.W., et al., eds., Pergamon Press, New York, NY, pp. 863-934 (1984).

Colatsky, T.J., et al., "Channel Specificity in Antiarrhythmic Drug Action: Mechanism of Potassium Channel Block and Its Role in Suppressing and Aggravating Cardiac Arrhythmias," *Circulation* 82:2235-2242, American Heart Association (1990).

Courtemanche, M., et al., "Ionic targets for drug therapy and atrial fibrillation-induced electrical remodeling: insights from a mathematical model," *Cardiovasc. Res.* 42:477-489, Elsevier Science B.V. (1999).

Fedida, D., et al., "Identity of a Novel Delayed Rectifier Current From Human Heart With a Cloned K$^+$ Channel Current," *Circ. Res.* 73:210-216, Lippincott Williams & Wilkins (1993).

Feng, J., et al., "Antisense Oligodeoxynucleotides Directed Against Kv1.5 mRNA Specifically Inhibit Ultrarapid Delayed Rectifier K$^+$ Current in Cultured Adult Human Atrial Myocytes," *Circ. Res.* 80:572-579, American Heart Association, Inc. (1997).

Feng, J., et al., "Effects of Class III Antiarrhythmic Drugs on Transient Outward and Ultra-rapid Delayed Rectifier Currents in Human Atrial Myocytes," *J. Pharmacol. Exp. Ther.* 281:384-392, American Society for Pharmacology and Experimental Therapeutics (1997).

Ford, J.W., et al., "Potassium Channels: Gene Family, Therapeutic Relevance, High-Throughput Screening Technologies and Drug Discovery," in *Progress in Drug Research, vol. 58*, Jucker, E., ed., Birkhauser Verlag, Boston, MA, pp. 133-168 (2002).

Godreau, D., et al., "Mechanisms of Action of Antiarrhythmic Agent Bertosamil on hKv1.5 Channels and Outward Potassium Current in Human Atrial Myocytes," *J. Pharmacol. Exp. Ther.* 300:612-620, American Society for Pharmacology and Experimental Therapeutics (2002).

Gutman, G.A., et al., "International Union of Pharmacology. XLI. Compendium of Voltage-Gated Ion Channels: Potassium Channels," *Pharmacol. Rev.* 55:583-586, American Society for Pharmacology and Experimental Therapeutics (Dec. 2003).

Hebert, S.C., "General Principles of the Structure of Ion Channels," *Am. J. Med.* 104:87-98, Excerpta Medica, Inc. (1998).

Hosni, H.M., et al., "Thienopyrimidines II: Synthesis of Newer Thieno[2,3-d]-Pyrimidines and Their Quaternized Derivatives with Molluscicidal Activity," *Acta Pol. Pharm.—Drug Res.* 56:49-56, Polish Pharmaceutical Society (1999).

Hozien, Z.A., et al., "Synthesis and Application of Some New Thienopyrimidine Dervatives as Antimicrobial Agents," *Synthetic Communications* 26:3733-3755, Marcel Dekker, Inc. (1996).

Ismail, K.A., et al., "Synthesis and Antimicrobial Activity of Some Tetiamethylenethieno[2,3-d]pyrimidine derivatives," *Il Farmaco* 50:611-616, Elsevier (1995).

Jordis, U., et al., "7,9-Dideaza-9-Thiaadenines (4-Aminothieno/2,3-d/pyritnidines) as Potential Anticytokinines," *Vestn. Slov. Kem. Drus.* 33:217-238, Drustvo (1986).

Katada, J., et al., "Cytotoxic effects of NSL-1406, a new thienopyrimidine derivative, on leukocytes and osteoclasts," *Bioorg. Med. Chem. Lett.* 9:797-802, Elsevier Science Ltd. (1999).

Knobloch, K., et al., "Electrophysiological and antiarrhythmic effects of the novel $I_{Kur}$ channel blockers, S9947 and S20951, on left vs. right pig atrium in vivo in comparison with the $I_{Kr}$ blockers dofetilide, azimilide, d,l-sotalol and ibutilide," *Naunyn-Schmiedeberg's Arch. Pharmacol.* 366:482-487, Springer-Verlag (2002).

Konno, S., et al., "Synthesis of Thienopyrimidine Derivatives and Their Antifungal Activities," *Yakugaku Zasshi* 109:464-473, Pharmaceutical Society of Japan (1989).

Li, G.-R., et al., "Evidence for Two Components of Delayed Rectifier K$^+$ Current in Human Ventricular Myocytes," *Circ. Res.* 78:689-696, American Heart Association, Inc. (1996).

Malayev, A.A., et al., "Mechanism of Clofilium Block of the Human Kv1.5 Delayed Rectifier Potassium Channel," *Mol. Pharmacol.* 47:198-205, American Society for Pharmacology and Experimental Therapeutics (1995).

Marbán, E., "Cardiac channelopathies," *Nature* 415:213-218, Macmillan Magazines Ltd. (2002).

Matsuda, T., et al., "Inhibition by a novel anti-arrhythmic agent, NIP-142, of cloned human cardiac K$^+$ channel Kv1.5 current," *Life Sci.* 68:2017-2024, Elsevier Science, Inc. (2001).

Moneer, A.A., et al., "Reaction of 3-Amino and 4-hydrazino-5,6-Tetramethylenethieno[2,3-d]Pyrimidine Derivatives with Azlactones," *Egypt. J. Pharm. Sci.* 34:599-609, National Information & Documentation Centre (1993).

Munchhof, M.J., et al., "Design and SAR of thienopyrimidine and thienopyridine inhibitors of VEGFR-2 kinase activity," *Bioorg. Med. Chem. Lett.* 14:21-24, Elsevier Ltd. (Jan. 2004).

Nakayama, J., "Thiophenes and their Benzo Derivatives: Synthesis," in *Comprehensive Heterocyclic Chemistry II, vol. 2*: Katritzky, A.R., et al., eds., pp. 607-677, Pergamon Press, New York, NY (1996).

Nattel, S., et al., "Cardiac Ultrarapid Delayed Rectifiers: A Novel Potassium Current Family of Functional Similarity and Molecular Diversity," *Cell Physiol. Biochem.* 9:217-226, S. Karger AG (1999).

Nattel, S., "Therapeutic implications of atrial fibrillation mechanisms: can mechanistic insights be used to improve AF management?," *Cardiovasc. Res.* 54:347-360, Elsevier Science B.V. (2002).

Noravyan, A.S., et al., "Synthesis and anticonvulsive activity of 4-alkyl (or aryl)amino-6,6-dimethyl-5,6-dihydro-8H-pyrano (or thiopyrano)[3,4-b]thieno[5,4-d] pyrimidines," *Khimiko-Farmatsevticheskii Zhurnal* 11:38-42, Folium Publishing Company (1977).

Peukert, S., et al., "Identification, Synthesis, and Activity of Novel Blockers of the Voltage-Gated Potassium Channel Kv1.5," *J. Med. Chem.* 46:486-498, American Chemical Society (Feb. 2003).

Ram, V.J., "Thieno[2,3-*d*]pyrimidines as Potential Chemotherapeutic Agents," *Arch. Pharm. (Weinheim)* 312:19-25, Verlag Chemie, GmbH (1979).

Ram, V.J., et al., "Thieno[2,3-*d*]pyrimidines as Potential Chemotherapeutic Agents. II," *J. Heterocylic Chem.* 18:1277-1280, HeteroCorporation (1981).

Shehata, I.A., et al., "Synthesis, Antitumor and Anti-HIV-1 Testing of Certain Thieno[2,3-*d*]pyrimidine, Thieno[2,3-*d*]imidazo[1,2-c]pyrimidine and Thieno[2,3-*d*] [1,3]thiazine Derivatives," *Med. Chem. Res.* 6:148-163, Birkhäuser Boston (1996).

Shieh, C.-C., et al., "Potassium Channels: Molecular Defects, Diseases, and Therapeutic Opportunities," *Pharmacol. Rev.* 52:557-593, American Society for Pharmacology and Experimental Therapeutics (2000).

(56) References Cited

OTHER PUBLICATIONS

Stewart, A.O., et al., "Discovery of Inhibitors of Cell Adhesion Molecule Expression in Human Endothelial Cells. 1. Selective Inhibition of ICAM-1 and E-Selectin Expression," *J. Med. Chem.* 44:988-1002, American Chemical Society (2001).
Tyle, P., "Iontophoretic Devices for Drug Delivery," *Pharm. Res.* 3:318-326, Plenum Publishing Corporation (1986).
Wang, Z., et al., "Sustained Depolarization-Induced Outward Current in Human Atrial Myocytes: Evidence for a Novel Delayed Rectifier $K^+$ Current Similar to Kv1.5 Cloned Channel Currents," *Circ. Res.* 73:1061-1076, American Heart Association (1993).
Wang, Z., et al., "Effects of Flecainide, Quinidine, and 4-Aminopyridine on Transient Outward and Ultrarapid Delayed Rectifier Currents in Human Atrial Myocytes," *J. Pharmacol. Exp. Ther.* 272:184-196 (1995).
Wirth, K.J., et al., "Atrial effects of the novel $K^+$-channel-blockers AVE0118 in anesthetized pigs," *Cardiovasc. Res.* 60:298-306, Elsevier B.V. (Nov. 2003).
Xu, D.H. and Xu, S.B., "The Expression of Arrhythmic Related Genes on *Xenopus* Oocytes for Evaluation of Class III Antiarrhythmic Drugs from Ocean Active Material," *Acta Genetica Sinica* 27:195-201, Science Press and Elsevier Press (2000).
Dialog File 351, Accession No. 607591, Derwent WPI English language abstract for JP 48-81892 (listed on accompanying PTO/SB/08A as document FP1).
Dialog File 351, Accession No. 607592, Derwent WPI English language abstract for JP 48-81893 (listed on accompanying PTO/SB/08A as document FP2).
Dialog File 351, Accession No. 3566123, Derwent WPI English language abstract for DD 226 893 A1 (listed on accompanying PTO/SB/08A as document FP10).
Dialog File 351, Accession No. 12964595, Derwent WPI English language abstract for DE 101 04 802 A1 (listed on accompanying PTO/SB/08A as document FP23).
STNEasy Database, Accession No. 1978:37739, English language abstract for Noravyan, A.S., et al., "Synthesis and anticonvulsive activity of 4-alkyl (or aryl)amino-6,6-dimethyl-5,6-dihydro-8H-pyrano (or thiopyrano)[3,4-b]thieno[5,4-d] pyrimidines," *Khimiko-Farmatsevticheskii Zhurnal* 11:38-42, Folium Publishing Company (1977).
Abdelrazek, F.M., et al., "Synthesis of Novel Thieno[2,3-*d*]pyrimidine, Thieno[2,3-*b*]pyridine and Thiazolo[3,2-*a*]thieno[2,3-*d*]pyrimidine Derivatives and their effect on the production of Mycotoxins," *Arch. Pharm. (Weinheim)* 325:301-306, VCH Verlagsgesellschaft mbH (1992).
Baell, J.B., et al., "Khellinone Derivatives as Blockers of the Voltage-Gated Potassium Channel Kv1.3: Synthesis and Immunosuppressive Activity," *J. Med. Chem.* 47:2326-2336, American Chemical Society (Apr. 2004).
Barker, J.M., et al., "Thienopyridines. Part 6. Synthesis and Nucleophilic Substitution of Some Chlorothieno[2,3-b]pyridine Derivatives, and Comparisons with the Analogous Quinoline Compounds," *J. Chem. Research (M)*:2501-2523, Science Reviews, Ltd. (1985).
Beeton, C., et al., "Selective blockade of T lymphocyte $K^+$ channels ameliorates experimental autoimmune encephalomyelitis, a model for multiple sclerosis," *Proc. Natl. Acad. Sci. USA* 98:13942-13947, National Academy of Sciences (2001).
Beeton, C., et al., "A Novel Fluorescent Toxin to Detect and Investigate Kv1.3 Channel Up-regulation in Chronically Activated T Lymphocytes," *J. Biol. Chem.* 278:9928-9937, American Society for Biochemistry and Molecular Biology, Inc. (Mar. 2003).
Boschelli, D.H., et al., "Identification of 7-Phenylaminothieno-[3,2-*b*]pyridine-6-carbonitriles as a New Class of Src Kinase Inhibitors," *J. Med. Chem.* 47:6666-6668, American Chemical Society (Dec. 2004).
Charvát, T., et al., "Diethyl Acetonedicarboxylate—a Precursor for the Synthesis of New Substituted 4-Aminoquinolines and Fused 4-Aminopyridines," *Monatshefie für Chemie* 126:333-340, Springer-Verlag (1995).

Desir, G.V., "Kv1.3 potassium channel blockade as an approach to insulin resistance," *Expert Opin. Ther. Targets* 9:571-579, Ashley Publications Ltd. (Jun. 2005).
Felix, J.P., et al., "Identification and Biochemical Characterization of a Novel Nortriterpene Inhibitor of the Human Lymphocyte Voltage-Gated Potassium Channel, Kv1.3," *Biochemistry* 38:4922-4930, American Chemical Society (1999).
Friedrich, M., et al., "Flow cytometric characterization of lesional T cells in psoriasis: intracellular cytokine and surface antigen expression indicates an activated, memory/ effector type 1 immunophenotype," *Arch. Dermatol. Res.* 292:519-521, Springer-Verlag (2000).
Gewald, K., et al., "Synthesen von 4-Amino-thieno[2,3-*b*]pyridinen," *Monatshefte für Chemie* 110:1189-1196, Springer-Verlag (1979).
Gilis, P.M., et al., "Synthesis and antibacterial evaluation of 4,7-dihydro-4-oxothieno[2,3-b] pyridine-5-carboxylic acids," *Eur. J. Med. Chem. Chim. Ther.* 13:265-269, Editions Scientifiques Elsevier (1978).
Hanson, D.C., et al., "UK-78,282, a novel piperidine compound that potently blocks the Kv1.3 voltage-gated potassium channel and inhibits human T cell activation," *Br. J. Pharmacol.* 126:1707-1716, Stockton Press (1999).
Leonard, R.J., et al., "Selective blockers of voltage gated $K^+$ channels depolarize human T lymphocytes: Mechanism of the antiproliferative effect of charybdotoxin," *Proc. Natl. Acad. Sci. USA* 89:10094-10098, National Academy of Sciences (1992).
Marco, J.L., et al., "Synthesis and Acetylcholinesterase/ Butyrylcholinesterase Inhibition Activity of 4-Amino-2,3-diaryl-5,6,7,8-tetrahydrofuro(and thieno)[2,3-*b*]-quinolines, and 4-Amino-5,6,7,8,9-pentahydro-2,3-diphenylcyclohepta[e]furo(and thieno)-[2,3-*b*] pyridines," *Arch. Pharm. Pharm. Med. Chem.* 335:347-353, Wiley-VCH GmbH & Co. (2002).
Meadows, H.J., et al., "Effect of SB-205384 on the decay of GABA-activated chloride currents in granule cells cultured from rat cerebellum," *Br. J. Pharmacol.* 121:1334-1338, Stockton Press (1997).
Nguyen, A., et al., "Novel Nonpeptide Agents Potently Block the C-Type Inactivated Conformation of Kv1.3 and Suppress T Cell Activation," *Mol. Pharmacol.* 50:1672-1679, American Society for Pharmacology and Experimental Therapeutics (1996).
O'Connor, K.C., et al., "The Neuroimmunology of Multiple Sclerosis: Possible Roles of T and B Lymphocytes in Immunopathogenesis," *J. Clin. Immunol.* 21:81-92, Plenum Publishing Corporation (2001).
Page, R.L. and Roden, D.M., "Drug Therapy for Atrial Fibrillation: Where Do We Go from Here?," *Nat. Rev. Drug Discov.* 4:899-910, Nature Publishing Group (Nov. 2005).
Schmitz, A., et al., "Design of PAP-1, a Selective Small Molecule Kv1.3 Blocker, for the Suppression of Effector Memory T Cells in Autoimmune Diseases," *Mol. Pharmacol.* 68:1254-1270, American Society for Pharmacology and Experimental Therapeutics (Nov. 2005).
Shah, K., et al., "Immunosuppressive effects of a Kv1.3 inhibitor," *Cell. Immunol.* 221:100-106, Elsevier Science (Feb. 2003).
Suzuki, M., et al., "Synthesis and Biological Evaluations of Condensed Pyridine and Condensed Pyrimidine-Based HMG-CoA Reductase Inhibitors," *Bioorg. Med. Chem. Lett.* 11:1285-1288, Elsevier Science Ltd (2001).
Valverde, P., et al., "Potassium Channel-blockers as Therapeutic Agents to Interfere with Bone Resorption of Periodontal Disease," *J. Dent. Res.* 84:488-499, International & American Associations for Dental Research (Jun. 2005).
Vennekamp, J., et al., "Kv1.3-Blocking 5-Phenylalkoxypsoralens: A New Class for Immunomodulators," *Mol. Pharmacol.* 65:1364-1374, American Society for Pharmacology and Experimental Therapeutics (Jun. 2004).
Viglietta, V., et al., "GAD65-reactive T cells are activated in patients with autoimmune type 1a diabetes," *J. Clin. Invest.* 109:895-903, American Society for Clinical Investigation (2002).
Wulff, H., et al., "Alkoxypsoralens, Novel Nonpeptide Blockers of *Shaker*-Type $K^+$ Channels: Synthesis and Photoreactivity," *J. Med. Chem.* 41:4542-4549, American Chemical Society (1998).

(56) References Cited

OTHER PUBLICATIONS

Wulff, H., et al., "Potassium channels as therapeutic targets for autoimmune disorders," *Curr. Opin. Drug Discov. Devel.* 6:640-647, Thomson Scientific (Sep. 2003).
Wulff, H., et al., "The voltage-gated Kv1.3 $K_+$ Channel in effector memory T cells as new targets for MS," *J. Clin. Invest.* 111:1703-1713, American Society for Clinical Investigation (Jun. 2003).
Wulff, H., et al., "$K^+$ Channel Expression during B Cell Differentiation: Implications for Immunomodulation and Autoimmunity," *J. Immunol.* 173:776-786, American Association of Immunologists, Inc. (Jul. 2004).
Xu, J., et al., "The voltage-gated potassium channel Kv1.3 regulates peripheral insulin sensitivity," *Proc. Natl. Acad. Sci. USA* 101:3112-3117, National Academy of Sciences (Mar. 2004).
Yamashita, K., et al., "Severe chronic graft-versus host disease is characterized by a preponderance of $CD4^+$ effector memory cells relative to central memory cells," *Blood* 103:3986-3988, American Society of Hematology (May 2004).
Yoon, J.-W. and Jun, H.-S., "Cellular and Molecular Pathogenic Mechanisms of Insulin-Dependent Diabetes Mellitus," *Ann. NY Acad. Sci.* 928:200-211, New York Academy of Sciences (2001).
International Search Report for International Application No. PCT/GB2004/002454, European Patent Office, Netherlands, mailed on Nov. 2, 2004.
Harb et al. STN Accession No. 1992:255564 Document No. 116:255564 Abstract of Bulletin of the Faculty of Science, Assiut University (1991), 20(2), 55-63.
Klem et al. STN Acession No. 1974:491385 Document No. 81:91385, Abstract of *Journal of Heterocyclic Chemistry* (1974), 11(3), 355-361 (1974).
Molina, P., et al., "An Efficient Iminophosphorane-Mediated Synthesis of Thieno[3,2-*c*]pyridine, Thieno[2,3-*c*]pyridine and Furo[3,2-*c*]-pyridine Derivatives," *Synthesis* 1:45-48, Thieme Chemistry (1987).
Pedersen et al. STN Acession No. 1978:50683 Document No. 88:50683, Abstract of *Tetrahedron* (1977), 33(16), 2089-92.
Shvedov et al. STN Acession No. 1974:95865 Document No. 80:95865, Abstract of *Khimiya Geterotsiklicheskikh* (1974), (1), 58-60.
International Search Report and Written Opinion for International Application No. PCT/GB2006/004594, European Patent Office, Netherlands, mailed on Jun. 19, 2007.
Dialog File 351, Accession No. 197029, Derwent WPI English language abstract for DE 19 65 710 (Listed on accompanying PTO/SB/08A form as document FP36).
Dialog File 351, Accession No. 1689342, Derwent WPI English language abstract for DE 28 31 677 A1 (Listed on accompanying PTO/SB/08A form as document FP38).
English language abstract for Japanese Application Publication JP 3254843 (cited on attached form PTO/SB/08A as document FP39) STN Acession No. 1995:846501 Document No. 123:256681.
English language abstract for Japanese Application Publication JP 07-076586 (cited on attached form PTO/SB/08A as document FP40) STN Acession No. 1995:662485 Document No. 123:55855.
Office Action for U.S. Appl. No. 11/297,330, Ford, J., et al., filed Dec. 9, 2005, mailed on May 1, 2008.
Office Action for U.S. Appl. No. 10/864,771, Ford, J., et al., filed Jun. 6, 2004, mailed on Jan. 23, 2008.
Office Action for U.S. Appl. No. 10/864,771, Ford, J., et al., filed Jun. 6, 2004, mailed on Apr. 5, 2007.
International Search Report for International Patent Application No. PCT/GB2005/004753, European Patent Office, Netherlands, mailed Mar. 22, 2006.
Klemm, L.H., et al., "Chemistry of Thienopyridines. VIII. Substitution Products Derived from Thieno [2,3-*b*] pyridine 7-Oxide (1)," *J. Heterocycl. Chem.* 7:81-89, Journal of Heterocyclic Chemistry (1970).
Klemm, L.H., and Merrill, R.E., "Chemistry of Thienopyridines. XIII. Selective Formation of Sulfones in Bi- and Tricyclic Systems. Thieno [2,3-*b*] pyridine 1,1-Dioxide as a Dienophile (1)," *J. Heterocycl. Chem.* 9:293-298, Journal of Heterocyclic Chemistry (1972).
Klemm, L.H., and Hartling, R., "Chemistry of Thienopyridines. XXIV. Two Transformations of Thieno [2,3-*b*] pyridine 7-Oxide (1)," *J. Heterocyclic Chem.* 13:1197-1200, Journal of Heterocyclic Chemistry (1976).
Sabnis, R.W., "The Gewald Synthesis," *Sulfur Reports* 16:1-17, Hardwood Academic Publishers GmbH (1994).
Schäfer, H., et al:, "2-Arylamino-thiophen-3-carbonsäurederivate," *J. F. Prakt. Chemie* 326:917-928, Johan Ambrosius Barth Leipzig (1984).
Gewald reaction, Wikipedia, http://en.wikipeida.org/wiki/Gewald_reaction, 2 pages, accessed on Aug. 22, 2008.
English-language translation of JP 48-81893, published Nov. 1, 1973, Hisamitsu Pharmaceutical Co., Ltd.
Moore, S., Office Action for U.S. Appl. No. 10/864,771, filed Jun. 10, 2004, U.S. Patent and Trademark Office, Alexandria, Virginia, mailed Feb. 4, 2009.
Moore, S., Advisory Action for U.S. Appl. No. 10/864,771, filed Jun. 10, 2004, U.S. Patent and Trademark Office, Alexandria, Virginia, mailed Aug. 1, 2008.
Chandrakumar, N. S., Notice of Allowance and Fee(s) Due for U.S. Appl. No. 11/297,330, filed Dec. 9, 2005, U.S. Patent and Trademark Office, Alexandria, Virginia, mailed Apr. 9, 2009.
Chandrakumar, N. S., Office Action for U.S. Appl. No. 11/297,330, filed Dec. 9, 2005, U.S. Patent and Trademark Office, Alexandria, Virginia, mailed Nov. 21, 2008.
Moore, S., Office Action for U.S. Appl. No. 10/864,771, filed Jun. 10, 2004, U.S. Patent and Trademark Office, Alexandria, Virginia, mailed Nov. 6, 2009.
Moore, S., Office Action for U.S. Appl. No. 10/864,771, filed Jun. 10, 2004, U.S. Patent and Trademark Office, Alexandria, Virginia, mailed Jul. 20, 2010.
Moore, S., Notice of Allowance for U.S. Appl. No. 10/864,771, filed Jun. 10, 2004, U.S. Patent and Trademark Office, Alexandria, Virginia, mailed May 19, 2011.
Boschelli, D.H. et al., "Inhibition of Src Kinase Activity by 4-Anilino-7-thienyl-3-quinolinecarbonitriles," *Bioorg. Med. Chem. Lett.* 12:2011, Elsevier Science Ltd. (2002).
Takada, S. et al., STN Accession No. 1998:724203, Document No. 130:38288, Abstract of Japanese Patent No. 10298180A, published Nov. 10, 1998.

\* cited by examiner

THIENO[3,2-C]PYRIDINE POTASSIUM CHANNEL INHIBITORS

CROSS REFERENCE TO RELATED APPLICATIONS

This application claims the benefit of U.S. Provisional Application No. 60/748,583 filed Dec. 9, 2005, the entirety of which is hereby incorporated by reference herein.

BACKGROUND OF THE INVENTION

1. Field of the Invention

The present invention relates to thienopyridine compounds which are potassium channel inhibitors. Pharmaceutical compositions comprising the compounds and their use in the treatment or prevention of cancer, arrhythmias, autoimmune diseases and inflammatory diseases, including gastric cancer, atrial fibrillation, type-2 diabetes mellitus, rheumatoid arthritis, type-1 diabetes, inflammatory bowel disorder and demyelinating disorders such as multiple sclerosis are also provided.

2. Background Art

Ion channels are proteins that span the lipid bilayer of the cell membrane and provide an aqueous pathway through which specific ions such as $Na^+$, $K^+$, $Ca^{2+}$ and $Cl^-$ can pass. Potassium channels represent the largest and most diverse sub-group of ion channels and they play a central role in regulating the membrane potential and controlling cellular excitability. Potassium channels have been categorized into gene families based on their amino acid sequence and their biophysical properties.

Compounds which modulate potassium channels have multiple therapeutic applications in several disease areas including cardiovascular, neuronal, auditory, renal, metabolic, immunosuppression and cell proliferation. More specifically potassium channels such as Kv4.3, Kir2.1, hERG, KvLQT1/MinK, $IK_{ACh}$, $IK_{Ado}$, $K_{ATP}$ and Kv1.5 are involved in the repolarisation phase of the action potential in cardiac myocytes. Furthermore channels such as Kv1.3 and IKCa1 are essential for maintaining the plasma membrane potential of numerous mammalian cells, including lymphocytes, the key effector cells of the adaptive immune system.

The human delayed rectifier voltage gated potassium channel subunit, Kv1.5, is exclusively expressed in atrial myocytes and is believed to offer therapeutic opportunities for the management of atrial fibrillation for several different reasons (see review, Brendel and Peukert, 2002): (i) There is evidence that Kv1.5 underlies the cardiac ultrarapid delayed rectifier ($Kv_{(ur)}$) physiological current in humans due to similar biophysical and pharmacological properties. This has been supported with antisense oligonucleotides to Kv1.5 which have been shown to reduce $Kv_{(ur)}$ amplitude in human atrial myocytes. (ii) electrophysiological recordings have demonstrated that $Kv_{(ur)}$ is selectively expressed in atrial myocytes, and therefore avoids inducing potentially fatal ventricular arrhythmia through interfering with ventricular repolarisation. (iii) Inhibiting $Kv_{(ur)}$ in atrial fibrillation-type human atrial myocytes prolonged the action potential duration compared to normal healthy human atrial myocytes. (iv) Prolonging the action potential duration by selectively inhibiting Kv1.5 could present safer pharmacological interventions for protecting against atrial re-entrant arrhythmias such as atrial fibrillation and atrial flutter compared to traditional class III antiarrythmics, by prolonging the atrial refractory period while leaving ventricular refractoriness unaltered. Class III antiarrythmics have been widely reported as a preferred method for treating cardiac arrhythmias.

Drugs that maintain cardiac sinus rhythm long-term without proarrhythmic or other side effects are highly desirable and not currently available. Traditional and novel class III antiarrythmic potassium channel blockers have been reported to have a mechanism of action by directly modulating Kv1.5 or $Kv_{(ur)}$. The known class III antiarrythmics ambasilide (Feng et al., 1997), quinidine (Wang et al., 1995), clofilium (Malayev et al., 1995) and bertosamil (Godreau et al., 2002) have all been reported as potassium channel blockers of $Kv_{(ur)}$ in human atrial myocytes. The novel benzopyran derivative, NIP-142, blocks Kv1.5 channels, prolongs the atrial refractory period and terminates atrial fibrillation and flutter in in vivo canine models, and S9947 inhibited Kv1.5 stably expressed in both *Xenopus oocytes* and Chinese hamster ovary (CHO) cells and $Kv_{(ur)}$ in native rat and human cardiac myocytes. Elsewhere, other novel potassium channel modulators which target Kv1.5 or $Kv_{(ur)}$ have been described for the treatment of cardiac arrhythmias, these include biphenyls (Peukert et al, 2003), thiophene carboxylic acid amides (WO0248131), bisaryl derivatives (WO0244137, WO0246162), carbonamide derivatives (WO0100573, WO0125189) anthranillic acid amides (WO2002100825, WO02088073, WO02087568), dihydropyrimidines (WO0140231), cycloalkylamine derivatives (WO2005018635), isoquionolines (WO2005030791), quinolines (WO2005030792), imidazopyrazines (WO2005034837), benzopyranols (WO2005037780), isoquinolinones (WO2005046578), cycloakyl derivatives (WO03063797), indane derivatives (WO0146155 WO9804521), tetralin benzocycloheptane derivatives (WO9937607), thiazolidone and metathiazanone derivatives (WO9962891), benzamide derivatives (WO0025774), isoquinoline derivatives (WO0224655), pyridazinone derivatives (WO9818475 WO9818476), chroman derivatives (WO9804542), benzopyran derivatives (WO0121610, WO03000675, WO0121609, WO0125224, WO02064581), benzoxazine derivatives (WO0012492), and the novel compound A1998 purified from Ocean material (Xu & Xu, 2000).

The Kv1.3 channel is expressed in both white and brown adipose tissue, and skeletal muscle. Inhibition of the channel potentiates the hypoglycemic action of insulin, through increased insulin-stimulated glucose uptake in these tissues. This is supported by in vivo data, showing that Kv1.3 inhibition in mice with type 2 diabetes mellitus were significantly more sensitive to insulin. There is strong evidence that Kv1.3 inhibition improves peripheral glucose metabolism by facilitating GLUT4 translocation to the plasma membrane of adipocytes and myocytes (Desir, 2005). Small molecule inhibitors of Kv1.3 are emerging as potential targets in the management of type-2 diabetes, through their actions as insulin sensitisers (WO02-100248).

Voltage gated potassium channels are thought to be involved in the proliferation of many types of cells including tumour cells. The neoplastic process may involve the overexpression of the Kv channels and the related channel activity. Changes in potassium channel expression have been implicated in gastric cancer (Lan et al 2005) and chronic prostatitis (Liang et al 2005). Potassium channels have also been shown to be associated with the proliferation of endothelial cells possibly as they play a role in cell cycle regulation (Erdogan et al 2004).

Human T lymphocytes possess two types of potassium channels: the voltage-gated potassium Kv1.3 and the $Ca^{2+}$-activated IKCa1 $K^+$ channels. These channels set the resting membrane potential of T-lymphocytes, playing a crucial role in the Ca$^{2+}$ signal transduction pathway that lead to activation of these cells following antigenic stimulation. Disruption of these pathways can attenuate or prevent the response of T-cells to antigenic challenge resulting in immune suppression.

The voltage-gated Kv1.3 and the Ca$^{2+}$-activated IKCa1 K$^+$ channels are expressed in T-cells in distinct patterns that accompany the proliferation, maturation and differentiation of these cells. The immunomodulatory effects of channel blockers depends on the expression levels of Kv1.3 and IKCa1 channels, which change dramatically when T-cells transition from resting to activated cells, and during differentiation from the naïve to the memory state. Kv1.3 channels dominate functionally in quiescent cells of all T-cell subtypes (naïve, $T_{CM}$ and $T_{EM}$). Activation has diametrically opposite effects on channel expression; as naïve and $T_{CM}$ cells move from resting to proliferating blast cells, they upregulate IKCa1 channels. Consequently activated naïve and $T_{CM}$ cells express ~500 IKCa1 channels and an approximately equivalent number of Kv1.3 channels. In contrast, activation of $T_{EM}$ cells enhances Kv1.3 expression without any change in IKCa1 levels. Functional Kv1.3 expression increases dramatically to 1500 Kv1.3 channels/cell, and their proliferation is sensitive to Kv1.3 blockers (Wulff et al., 2003). B-cells also show a switch in K$^+$ channel during differentiation that parallels the changes seen in the T-cell lineage (Wulff et al., 2004). The discovery that the majority of myelin-reactive T-cells in patents with MS are Kv1.3$^{high}$ $T_{EM}$ cells has raised interest in the therapeutic potential of Kv1.3 blockers in autoimmune disorders. Kv1.3 blockers have been shown to ameliorate adoptive EAE induced by myelin-specific memory T-cells (a model for MS) and to prevent inflammatory bone resorption in experimental periodontal disease caused mainly by memory cells. In addition, there is increasing evidence implicating late memory cells in the pathogenesis of type-1 diabetes, rheumatoid arthritis, psoriasis, inflammatory bowel disorder, Crohn's disease, Grave's disease, Plummer's disease, systemic lupus erythematosus, chronic graft rejection and chronic graft-vs-host disease. Specific Kv1.3 blockers might therefore constitute a new class of memory-specific immunomodulators.

Numerous novel small molecule Kv1.3 channel blockers have been reported for the management of autoimmune disorders. These include the iminodihydroquinolines WIN173173 and CP339818 (Nguyen et al., 1996), the benzhydryl piperidine UK-78,282 (Hanson et al. 1999), correolide (Felix et al., 1999), cyclohexyl-substituted benzamide PAC (US-06194458, WO0025774), sulfamidebenzamidoindane (US-06083986), Khellinone (Baell et al., 2004), dichloropenylpyrazolopyrimidine (WO-00140231) and psoralens (Schmitz et al., 2005).

Thienopyridines have been reported to be useful as 5-HT receptor modulators and phosphatase and kinase inhibitors amongst others.

Thienopyridines substituted at the 2-position by alkyl, aryl, halogen, hydrogen or arylthioxy groups, the 4-position by alkyl, aryl, cyano, halogen and heteroaryl groups, in the 6-position by a secondary amide group and the 7-position by hydroxyl have been claimed as hypoxia inducible factor (HIF) modulators (WO2006094292).

Thienopyridines substituted at the 4-position by an amino group and at the 7-position by an aryl group have been claimed as inhibitors of kinases, in particular COT and MK2 kinases for the treatment of protein kinase-related diseases (WO2005110410).

Thienopyridines substituted at the 3-position by an alkyl or aryloxymethyl group, at the 4-position by an amino group and at the 7-position by a carboxamide, secondary amide or ester group have been claimed as KDR and FGFR kinase inhibitors for the treatment of cancer (US2005256154).

Thienopyridines substituted at the 2-position by an amide, carboxy or ester group, at the 3-position by an alkoxy group, at the 4-position by a hydrogen or halogen and at the 6-position by an alkyl substituent have been claimed as protein tyrosine phosphatase 1B inhibitors for treating diabetes and related diseases (WO2005081960).

Thienopyridines substituted at the 2-position by a hydrogen or alkyl group, at the 3-position by hydrogen, alkyl or heteroaryl groups, at the 4-position with an amino group and at the 7-position by hydrogen, halogen, aryl, heteroaryl, carboxy and secondary or tertiary amino groups have been claimed as tyrosine kinase inhibitors, useful for treating and preventing tumors and cancers (US2005043347, US2005026944, US2005020619, WO2004100947).

Thienopyridines substituted at the 2-position by an aryl group, at the 3-position by hydrogen or an alkyl group, at the 4-position by an amino group and at the 7-position by a carboxamide group have been claimed as IKKβ enzyme inhibitors for the treatment of inflammatory, immunoregulatory, metabolic, infectious and cell proliferative diseases or conditions (WO2005105809, US2004097485).

Thienopyridines substituted at the 2-position by a hydrogen or halogen group, 3-position by a halogen or sulfonamido group, 4-position by a piperazinyl group have been claimed as having inhibitory activities on 5-HT1A, 5-HT3 an 5-HT6 receptors, and are useful for the treatment of conditions relating to obesity, type-2 diabetes and CNS disorders (WO2005082887).

Thienopyridines substituted at the 2-position by hydrogen, 3-position by a heteroaryl group, 4-position by an amino group have been claimed as inhibitors of trypsin-like serine protease enzymes, and are useful as anticoagulant agents for treatment and prevention of thromboembolic disorders (WO0039108).

Thienopyridines substituted at the 2-position by an ester group, 3-position by an amino group and 4-position by an alkoxy group have been claimed as α1 adrenergic antagonists (U.S. Pat. No. 6,046,207).

Thienopyridines substituted at the 2-position by a hydrogen, halogen or cyano group, 3-position by a hydrogen or cyano group and at the 4-position by an oxypropanol derivative group have been claimed as useful adrenergic β-blocking agents, hypolidemics, hypoglycemics and antiarrhythmics (DE77-2703888, US75-605972, DE75-2536675).

BRIEF SUMMARY OF THE INVENTION

This invention provides compounds that are potassium channel inhibitors. These compounds are particularly useful for inhibiting the voltage-gated potassium channels, and in particular Kv1.3 and Kv1.5. These channels constitute known targets for the treatment of arrhythmias, type-2 diabetes mellitus and immunological disorders (Page and Rodin, 2005; Xu et al., 2004; Wulff et al., 2003b; O'Connor et al., 2001). This invention is not limited to treating arrhythmias, type-2 diabetes mellitus or immunological disorders, the compounds also being useful to treat diseases which require potassium channel inhibition (e.g. Shieh et al., 2000; Ford et al., 2002, Xie et al, 2004).

DETAILED DESCRIPTION OF THE INVENTION

Thus, in a first aspect, the present invention provides a compound of formula (I).

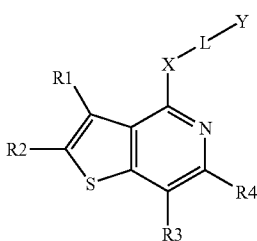

Wherein

R1 is H, NR5R6, NC(O)R7, halo, trifluoromethyl, cycloalkyl, alkyl, nitro, CONR5R6, CO$_2$R7, nitrile, alkoxy, aryl or heteroaryl;

R2 is H, NR5R6, NC(O)R7, halo, trifluoromethyl, cycloalkyl, alkyl, nitro, CONR5R6, CO$_2$R7, nitrile, alkoxy, aryl or heteroaryl;

R3 and R4 are H, NR5R6, NC(O)R7, halo, trifluoromethyl, alkyl, CONR5R6, CO$_2$R7, nitrile, alkoxy, aryl or heteroaryl;

R5 and R6 may be the same or different, and may be H, alkyl, aryl, heteroaryl or cycloalkyl; or R5 and R6 may together form a saturated, unsaturated or partially saturated 4 to 7 member ring, wherein said ring may optionally comprise one or more further heteroatoms selected from N, O or S;

R7 is H, alkyl, aryl, heteroaryl or cycloalkyl.

X is O, S or NR8;

R8 is H or alkyl;

L is (CH$_2$)$_n$, where n is 0, 1, 2, 3 or 4;

Y is alkyl, alkenyl, aryl, aryloxy, cycloalkyl, heteroaryloxy or heterocyclic group;

the products of oxidation of sulphur and/or nitrogen moieties on these molecules;

or pharmaceutically acceptable salts thereof.

As used herein, an alkyl group or moiety is typically a linear or branched alkyl group or moiety containing from 1 to 6 carbon atoms, such as a $C_1$-$C_4$ alkyl group or moiety, for example methyl, ethyl, n-propyl, i-propyl, butyl, i-butyl and t-butyl. An alkyl group or moiety may be unsubstituted or substituted at any position. Typically, it is unsubstituted or carries one or two substituents. Suitable substituents include halogen, cyano, nitro, alkoxy, hydroxyl, unsubstituted aryl, unsubstituted heteroaryl, aryloxy, heteroaryloxy, CO$_2$R7, C(O)NR9R10, NC(O)R7 and SO$_2$NR9R10.

As used herein, an aryl group is typically a $C_6$-$C_{10}$ aryl group such as phenyl or napthyl. A preferred aryl group is phenyl. An aryl group may be unsubstituted or substituted at any position. Typically, it carries 1, 2, 3 or 4 substituents. Suitable substituents include cyano, halogen, nitro, trifluoromethyl, alkyl, alkylthio, alkoxy, NR9R10, CO$_2$R7, C(O)NR9R10, NC(O)R7 and SO$_2$NR9R10 and hydroxyl.

As used herein, a heterocyclic group is a heteroaryl group, typically a 5- to 10-membered aromatic ring, such as a 5- or 6-membered ring, containing at least one heteroatom selected from O, S and N. Examples include pyridyl, pyrazinyl, pyrimidinyl, pyridazinyl, furanyl, thienyl, pyrazolidinyl, pyrrolyl and pyrazolyl groups. Preferred heteroaryl groups are furanyl, thienyl and pyridyl. Examples of polycyclic heterocycles include indolyl, benzofuranyl, benzothiophenyl and benzodioxolyl. Non-aryl heterocyclic groups are also included, such as tetrahydrofuranyl or pyrrolidinyl. A heterocyclic group may be unsubstituted or substituted at any position. Suitable substituents include cyano, nitro, halogen, alkyl, alkylthio, alkoxy, NR9R10, CO$_2$R7, C(O)NR9R10, NC(O)R7 and SO$_2$NR9R10 and hydroxyl.

R9 and R10 can be the same or different, and may be selected from H, unsubstituted alkyl, unsubstituted aryl, unsubstituted heteroaryl, unsubstituted cycloalkyl, aminoethyl, methylaminoethyl, dimethylaminoethyl, hydroxyethyl, alkoxyethyl, or R9 and R10 may together form a saturated, unsaturated or partially saturated 4 to 7 member ring.

When R5 and R6 or R9 and R10 together form a saturated, unsaturated or partially saturated 4 to 7 member ring, the ring may optionally comprise one, two, or three further heteroatoms.

As used herein, alkoxy means $C_{1-3}$ alkoxy, cycloalkyl means $C_{3-6}$ cycloalkyl and halogen means Cl, F, Br or I, preferably Cl, F or Br.

Compounds where oxidation of sulphur and/or nitrogen moieties has happened are also described. The person skilled in the art would understand that this term means, as used herein, that mono- or di-oxidation of sulphur moiety and/or mono-oxidation of the nitrogen moiety within the ring structure of the compound has occurred. Preferred compounds of formula I wherein mono- and di-oxidation of sulphur and/or mono-oxidation of nitrogen moieties in the compounds has taken place are also provided. Thus, compounds of formula I wherein the thieno[3,2c]pyridine moiety has been oxidized to one of the following are provided:

Thieno[3,2c]pyridine-1-oxide;
Thieno[3,2c]pyridine-1,1,-dioxide;
Thieno[3,2c]pyridine-1,1,5,-trioxide;
Thieno[3,2c]pyridine-1,5,-dioxide; and
Thieno[3,2c]pyridine-5-oxide.

Preferred compounds of formula I are those wherein R1 is aryl or heteroaryl; R2 is H or alkyl; R3 and R4 are H, alkyl, alkoxy, aryl, NR5R6, NC(O)R7, CONR5R6; X is O or NR8; R8 is H; n is 0, 1, 2, 3 or 4 and Y is alkyl, alkenyl, aryl, aryloxy, heteroaryloxy, cycloalkyl or heteroaryl. Particularly preferred compounds are those wherein R1 is aryl or heteroaryl; R2 is H or alkyl; R3 and R4 are H, alkyl, aryl, alkoxy, NR5R6; X is O or NR8; R8 is H; n is 0, 1, 2, 3 or 4 and Y is aryl or heteroaryl.

Preferred compounds include:
(3-Phenyl-thieno[3,2-c]pyridin-4-yl)-pyridin-2ylmethyl-amine;
(2,3-Dihydro-benzo[1,4]dioxin-6-ylmethyl)-[3-(4-fluoro-phenyl)-thieno[3,2-c]pyridin-4-yl]-amine;
(2,3-Dihydro-benzo[1,4]dioxin-6-ylmethyl)-(3-phenyl-thieno[3,2-c]pyridin-4-yl)-amine;
(2,3-Dihydro-benzo[1,4]dioxin-6-ylmethyl)-[3-(3-methoxy-phenyl)-thieno[3,2-c]pyridin-4-yl)-amine;
(3-Benzo[1,3]dioxol-5-yl-thieno[3,2-c]pyridin-4-yl)-(2,3-dihydro-benzo[1,4]dioxin-6-ylmethyl)-amine;
Benzyl-(3-phenyl-thieno[3,2-c]pyridin-4-yl)-amine;
Benzyl-[3-(4-fluoro-phenyl)-thieno[3,2-c]pyridin-4-yl]-amine;
Benzyl-[3-(3-methoxy-phenyl)-thieno[3,2-c]pyridin-4-yl]-amine;
Benzyl-(3-p-tolyl-thieno[3,2-c]pyridin-4-yl)-amine;
(3-Benzo[1,3]dioxol-5-yl-thieno[3,2-c]pyridin-4-yl)-benzyl-amine;
[3-(3-Methoxy-phenyl)-thieno[3,2-c]pyridin-4-yl]-thiophen-2-ylmethyl-amine;
(3-Phenyl-thieno[3,2-c]pyridin-4-yl)-thiophen-2-ylmethyl-amine;
[3-(4-Fluoro-phenyl)-thieno[3,2-c]pyridin-4-yl]thiophen-2-ylmethyl-amine;
(3-Benzo[1,3]dioxol-5-yl-thieno[3,2-c]pyridin-4-yl)-thiophen-2-ylmethyl-amine;
Furan-2-ylmethyl-(3-phenyl-thieno[3,2-c]pyridin-4-yl)amine;

[3-(4-Fluoro-phenyl)-thieno[3,2-c]pyridin-4-yl]-furan-2-yl-methyl-amine;
Furan-2-ylmethyl-[3-(3-methoxy-phenyl)-thieno[3,2-c]pyridin-4-yl]-amine;
Furan-2-ylmethyl-(3-p-tolyl-thieno[3,2-c]pyridin-4-yl)-amine;
(4-Phenyl-butyl)-(3-phenyl-thieno[3,2-c]pyridin-4-yl)-amine;
(3-Methyl-pyridin-2-ylmethyl)-(3-phenyl-thieno[3,2-c]pyridin-4-yl)-amine;
Benzyl-(3,7-di-p-tolyl-thieno[3,2-c]pyridine-4-yl)-amine;
Benzyl-(7-phenyl-3-p-tolyl-thieno[3,2-c]pyridine-4-yl)-amine;
2-(4-Benzylamino-3-p-tolyl-thieno[3,2-c]pyridin-7-yl)-phenol;
3-(4-Benzylamino-3-p-tolyl-thieno[3,2-c]pyridin-7-yl)-phenol;
4-(4-Benzylamino-3-p-tolyl-thieno[3,2-c]pyridin-7-yl)-phenol;
3-(4-Benzylamino-3-p-tolyl-thieno[3,2-c]pyridin-7-yl)-benzoic acid;
Benzyl-(7-pyridin-3-yl-3-p-tolyl-thieno[3,2-c]pyridin-4-yl)-amine;
Benzyl-(7-pyridin-4-yl-3-p-tolyl-thieno[3,2-c]pyridin-4-yl)-amine;
Benzyl-[7-(3-methanesulfonyl-phenyl)-3-p-tolyl-thieno[3,2-c]pyridin-4-yl]-amine;
Benzyl-[7-(4-dimethylamino-phenyl)-3-p-tolyl-thieno[3,2-c]pyridin-4-yl]-amine;
Benzyl-[7-(2-fluoro-phenyl)-3-p-tolyl-thieno[3,2-c]pyridin-4-yl]-amine;
Benzyl-[7-(3-fluoro-phenyl)-3-p-tolyl-thieno[3,2-c]pyridin-4-yl]-amine;
Benzyl-[7-(4-fluoro-phenyl)-3-p-tolyl-thieno[3,2-c]pyridin-4-yl]-amine;
Benzyl-(6-methyl-3-phenyl-thieno[3,2-c]pyridin-4-yl)-amine;
and pharmaceutically acceptable salts thereof.

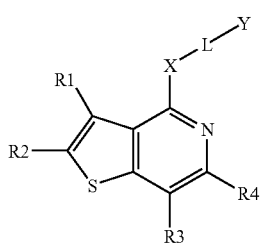

I

Compounds of formula I wherein R1 is aryl or heteroaryl may be synthesised by reaction of compounds of formula II by a coupling reaction using a suitable boronic acid, triphenylphosphine and palladium catalyst such as palladium (II) acetate in the presence of a solvent and a base. Preferably the solvent is a mixture of 1,2-dimethoxyethane and water, and the base is sodium carbonate. This reaction may optionally be carried out under sealed conditions and with microwave irradiation at a temperature 150-160° C. Compounds where R1 is a group other than aryl or heteroaryl could be prepared from the bromo intermediate using methods familiar to those skilled in the art, such as coupling with an alkene and formation of Grignard reagents and alkylation or acylation thereof.

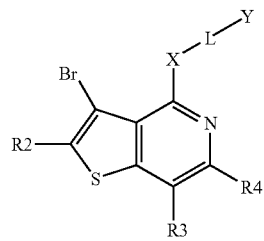

II

Compounds of formula II may be synthesized by reaction of compounds of formula III with a suitable nucleophile X-L-Y, where X, L and Y are as defined herein, optionally in the presence of a solvent and a base, and optionally at elevated temperature or with microwave irradiation. Preferably the solvent is N-methyl pyrrolidinone or anhydrous ethanol and the base is a hindered nitrogen base such as triethylamine. If a solvent is present the reaction is carried out at the reflux temperature of the solvent, or under sealed conditions and with microwave irradiation at elevated temperatures.

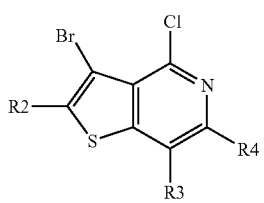

III

Compounds of formula III may be synthesized by reaction of a compound of formula IV with a chlorinating reagent such as phosphorous oxychloride or diphenyl phosphinic chloride at reflux temperature.

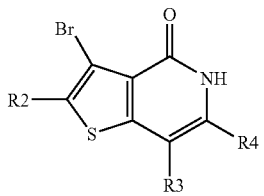

IV

Compounds of formula IV may be synthesized from compounds of formula V by heating in an organic solvent, preferably diphenyl ether, at reflux temperature.

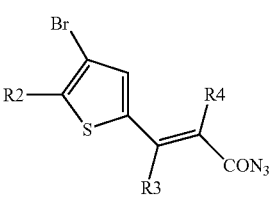

V

Compounds of formula V may be obtained by acid azide formation from compounds of formula VI. This may be performed at low temperature, in the presence of sodium azide, preferably in the presence of a solvent, and preferably in the presence of a base. Preferably the solvent is a mixture of acetone and ethyl chloroformate and the base is an organic nitrogen base such as triethylamine.

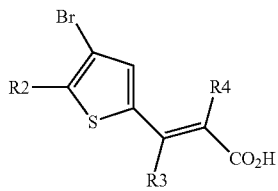

VI

Compounds of formula VI may be synthesized from compounds of formula VII by the reaction of a diacid at elevated temperature in a suitable solvent, preferably pyridine and an organic base, preferably piperidine. Suitable diacids include malonic acid.

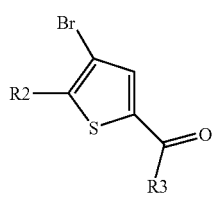

VII

Compounds of formula VII are widely available from commercial sources or can be readily synthesised using standard synthetic organic chemistry procedures.

Compounds of formula I wherein R3 is aryl may be synthesized by reaction of compounds of formula VIII by a coupling reaction using a suitable boronic acid, triphenylphosphine and palladium catalyst such as palladium (II) acetate in the presence of a solvent and a base. Preferably the solvent is a mixture of 1,2-dimethoxyethane and water, and the base is sodium carbonate. This reaction may optionally be carried out under sealed conditions and with microwave irradiation at a temperature of 150° C.

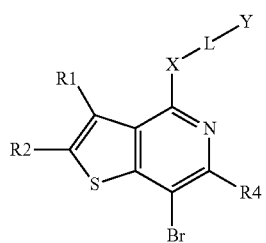

VIII

Compounds of formula VIII may be synthesized by reaction of compounds of formula I where R3 is H by bromination using N-bromosuccinimide at low temperature in the presence of a solvent, preferably tetrahydrofuran.

Compounds of formula I wherein R1 is aryl and R4 is alkyl, may also be synthesised from compounds of formula IX with a suitable nucleophile X-L-Y, where X, L and Y are as defined herein, in the presence of a solvent and a base, and with microwave irradiation at a temperature of 220° C. Preferably the solvent is N-methyl pyrrolidinone and the base is a hindered nitrogen base such as triethylamine.

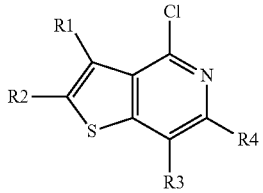

IX

Compounds of formula IX may be synthesized by reaction of a compound of formula X with a chlorinating reagent such as phosphorous oxychloride at reflux temperature.

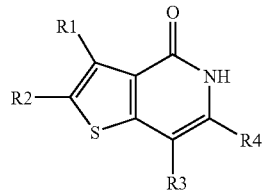

X

Compounds of formula X may be synthesized from compounds of formula XI by heating in an organic solvent, preferably toluene followed by 1,2-dichlorobenzene, at reflux temperature.

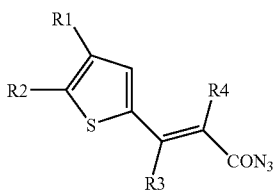

XI

Compounds of formula XI may be obtained by acid azide formation from compounds of formula XII. This may be performed at low temperature, in the presence of diphenylphosphoryl azide, preferably in the presence of a solvent, and preferably in the presence of a base. Preferably the solvent is tetrahydrofuran and the base is an organic nitrogen base such as triethylamine.

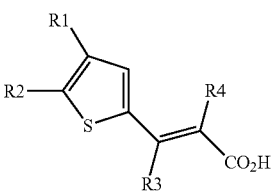

XII

Compounds of formula XII may be synthesised from compounds of formula XIII by the reaction of a bromoalkyl acid in the presence of base and solvent, preferably sodium hydride and 1,2-dimethoxyethane respectively. Suitable bromoalkyl acids include 2-bromopropionic acid.

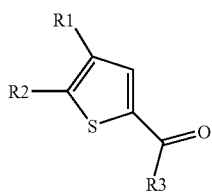

Compounds of formula XIII are widely available from commercial sources or can be readily synthesised using standard synthetic organic chemistry procedures.

Many of the starting materials referred to in the reactions described above are available from commercial sources or can be made by methods cited in the literature references. Synthetic methods for thienopyridines may be found in references such as Eloy et al (1970) and Bisagni et al (1974), WO2004-US13668, US2003-666857 and articles cited therein. Synthetic methods can also be found in reviews; thiophenes for example can be found in references cited in Comprehensive Heterocyclic Chemistry, Eds Katritzky, A. R., Rees, C. R., (4), 863-934, and Comprehensive Heterocyclic Chemistry (II), Eds Katritzky, A. R., Rees, C. W., Scriven, E. F. V., (2). 607-678.

Suitable starting materials include:

| Material | Reference | Supplier |
| --- | --- | --- |
| 4-Bromo-2-thiophenecarboxaldehyde | 283452 | Aldrich |
| 2-Picolylamine | A65204 | Aldrich |
| 2,3-Dihydro-1,4-benzodioxin-6-yl-methylaminebenzylamine | CC01313 | Acros |
| Benzylamine | 407712 | Aldrich |
| 2-Thiophenemethylamine | 220884 | Aldrich |
| Furfurylamine | F20009 | Aldrich |
| 2-Aminomethyl-3-methylpyridine | 20197 | Fluorochem |
| Phenylboronic acid | P20009 | Aldrich |
| 2-Hydroxybenzeneboronic acid | X19400G0001 | Lancaster |
| 3-Hydroxybenzeneboronic acid | 523968 | Aldrich |
| 4-Hydroxybenzeneboronic acid | 523976 | Aldrich |
| 3-Carboxyphenylboronic acid | 456764 | Aldrich |
| 3,4-(Methylenedioxy)phenylboronic acid | 499994 | Aldrich |
| Pyridine-3-boronic acid | X15040G0001 | Lancaster |
| Pyridine-4-carboxylic acid | X15179G0001 | Lancaster |
| (3-Methylsulfonylphenyl)boronic Acid | OR10565 | Apollo-Inter |
| 4-(Dimethylamino)phenylboronic acid | 483532 | Aldrich |
| 2-Fluorophenylboronic acid | 445223 | Aldrich |
| 3-Fluorophenylboronic acid | 441643 | Aldrich |
| 4-Fluorophenylboronic acid | 417556 | Aldrich |
| 3-Methoxyphenylboronic acid | 441686 | Aldrich |
| p-Tolylboronic acid | 393622 | Aldrich |
| 2-Bromopropionic acid | 241199 | Aldrich |
| 4-Phenylthiophene-2-carboxaldehyde | 569526 | Aldrich |

As discussed herein, the compounds of the invention are useful in the treatment of various conditions. Thus, in a second aspect, the present invention provides a compound of formula I as defined herein for use in medicine. In a further aspect the present invention provides a pharmaceutical formulation comprising at least one compound of formula I or as defined herein and optionally one or more excipients, carriers or diluents.

The compositions of the invention may be presented in unit dose forms containing a predetermined amount of each active ingredient per dose. Such a unit may be adapted to provide 5-100 mg/day of the compound, preferably either 5-15 mg/day, 10-30 mg/day, 25-50 mg/day 40-80 mg/day or 60-100 mg/day. For compounds of formula I, doses in the range 100-1000 mg/day are provided, preferably either 100-400 mg/day, 300-600 mg/day or 500-1000 mg/day. Such doses can be provided in a single dose or as a number of discrete doses. The ultimate dose will depend on the condition being treated, the route of administration and the age, weight and condition of the patient and will be at the doctor's discretion.

The compositions of the invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For applications to the eye or other external tissues, for example the mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administration to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Preferred unit dosage formulations are those containing a daily dose or sub-dose, as herein above recited, or an appropriate fraction thereof, of an active ingredient.

It should be understood that in addition to the ingredients particularly mentioned above, the formulations may also include other agents conventional in the art having regard to the type of formulation in question, for example those suitable for oral administration may include flavouring agents.

The compositions of the invention can be used to treat conditions which require inhibition of potassium channels, for example in the treatment of arrhythmias, type-2 diabetes, immunological disorders or cancer, in particular gastric cancer. Thus, in further aspects, the present invention provides:

(i) A method of treating or preventing a disorder which requires potassium channel inhibition, eg arrhythmia, type-2 diabetes, immunological disorders or cancer, in particular gastric cancer, comprising administering to a subject an effective amount of at least one compound of the invention or a pharmaceutical composition of the invention and (ii) the use of a compound of the invention in the manufacture of a medicament for use in potassium channel inhibition.

In particular, the medicament is for use in the treatment or prevention of arrhythmia, type-2 diabetes, immunological disorders or cancer, in particular gastric cancer.

EXAMPLES

Using the information outlined herein the following compounds can be synthesised which are given by way of example only. The pharmacological profile of compounds of the present invention can readily be assessed by those skilled in the art using routine experimentation, such as procedures and techniques illustrated herein and described in detail in Ford et al., 2002.

Example 1

(E)-3-(4-Bromo-thiophen-2-yl)-acrylic acid

4-Bromothiophenecarboxaldehyde (2.5 g, 13.1 mmol) was placed in a 25 ml round bottomed flask and charged with piperidine (0.14 ml, 0.11 mmol) and pyridine (7.1 ml). Malonic acid was then added (2.21 mg, 21.2 mmol) and the reaction heated to 100° C. and maintained for 24 h. The reaction was then allowed to cool to room temperature and the solvent removed in vacuo. The remaining residue was acidified with concentrated HCl to pH 3 and the solid collected, filtered and washed with distilled water (20 ml). It was then air and oven dried to yield a yellow solid (3.04 g, 100%).

Example 2

(E)-3-(4-Bromo-thiophen-2-yl)-acryloyl azide

A suspension of (E)-3-(4-bromo-thiophen-2-yl)-acrylic acid (3.0 g, 12.9 mmol) in anhydrous acetone (20 ml) was cooled in an ice-bath to 0° C. and treated with triethylamine (2.15 ml, 15.4 mmol) and ethyl chloroformate (1.24 ml, 15.4 mmol). The reaction was left to stir for 0.5 h before being treated with a solution of sodium azide (1.0 g, 15.4 mmol) in distilled water (4 ml). After stirring for 1 h at 0° C., the reaction was further diluted with distilled water (40 ml) and extracted with DCM (3×25 ml). The organic layer was dried ($MgSO_4$) and filtered for direct use in the next reaction.

Example 3

3-Bromo-5H-thieno[3,2-c]pyridine-4-one

Diphenyl ether (40 ml) was heated to boiling (bp. 259° C.) and treated cautiously with a crude solution of (E)-3-(4-bromo-thiophen-2-yl)-acryloyl azide. The volatiles were distilled off during the slow addition and the reaction heated for an additional 1 h. The reaction was then allowed to cool to room temperature and diluted with petroleum spirit 40-60° C. (100 ml) to afford a precipitate which was filtered, washed with hot petroleum spirit 40-60° C. (20 ml), and air and oven dried to yield a yellow solid (1.16 g, 39%).

Example 4

3-Bromo-4-chloro-thieno[3,2-c]pyridine

A stirred mixture of 3-bromo-5H-thieno[3,2-c]pyridine-4-one (1.16 g, 5.04 mmol) and phosphorus oxychloride (20 ml) was heated to reflux for 4 h. The reaction was then allowed to cool to room temperature and the phosphorus oxychloride removed in vacuo. The residue was dissolved in DCM (25 ml) and washed with distilled water (2×25 ml) followed by saturated sodium hydrogen carbonate solution (25 ml). The organic layer was dried ($MgSO_4$), filtered and the solvent removed in vacuo. The crude residue was then subjected to flash column chromatography (eluent petroleum spirit 40-60° C.:EtOAc, 5:1, $R_f$ 0.5) to afford the title compound as a yellow solid (398 mg, 32%).

Example 5

(3-Bromo-thieno[3,2-c]pyridin-4-yl)-pyridin-2-ylmethyl-amine

3-Bromo-4-chloro-thieno[3,2-c]pyridine (409 mg, 16.5 mmol) was dissolved in anhydrous EtOH (20 ml), and 2-picolylamine (184 µl, 17.9 mmol) and triethylamine (241 µl, 17.3 mmol) were added. The reaction was heated to reflux and this was maintained for 24 h. The reaction was then allowed to cool to room temperature. The solvent was removed in vacuo and the residue partitioned between DCM (20 ml) and a saturated sodium, chloride solution (20 ml). The organic layer was dried ($MgSO_4$), filtered and the solvent removed in vacuo. The crude residue was subjected to flash column chromatography (eluent petroleum spirit 40-60° C.:EtOAc, 3:1, $R_f$ 0.3). This afforded the title compound as a yellow solid (236 mg, 44%).

Example 6

(3-Bromo-thieno[3,2-c]pyridin-4-yl)-(2,3-dihydro-benzo[1,4]dioxin-6-ylmethyl)-amine A stirred mixture of 3-bromo-4-chloro-thieno[3,2-c]pyridine (200 mg, 0.80 mmol), 2,3-dihydro-1,4-benzodioxin-6-yl-methylaminebenzylamine (266 mg, 1.61 mmol), and triethylamine (112 μl, 0.80 mmol) in NMP (2 ml) was heated in a Biotage microwave reactor for 2 h at 220° C. At which point the reaction was allowed to cool to room temperature and partitioned between EtOAc (10 ml) and distilled water (10 ml). The organic layer was separated and washed with additional portions of distilled water (2×10 ml), dried (MgSO$_4$), filtered and the solvent removed in vacuo. The crude residue was then subjected to flash column chromatography (eluent petroleum spirit 40-60° C.:EtOAc, 3:1, R$_f$ 0.6). This afforded the title compound as a yellow solid (233 mg, 77%).

Examples 7 to 11

The compounds set out below were prepared in the same way as in Example 6, using the appropriate starting materials.

| Example | Compound |
|---|---|
| 7 | Benzyl-(3-bromo-thieno[3,2-c]pyridin-4-yl)-amine |
| 8 | (3-Bromo-thieno[3,2-c]pyridin-4-yl)-thiophen-2-ylmethyl-amine |
| 9 | (3-Bromo-thieno[3,2-c]pyridin-4-yl)-furan-2-ylmethyl-amine |
| 10 | (3-Bromo-thieno[3,2-c]pyridin-4-yl)-(4-phenyl-butyl)-amine |
| 11 | (3-Bromo-thieno[3,2-c]pyridin-4-yl)-(3-methyl-pyridin-2-ylmethyl)-amine |

Example 12

(3-Phenyl-thieno[3,2-c]pyridin-4-yl)-pyridin-2ylmethyl-amine

A microwave reaction vessel was charged with (3-bromo-thieno[3,2-c]pyridin-4-yl)-pyridin-2-ylmethyl-amine (50 mg, 0.158 mmol), phenylboronic acid (37.9 mg, 0.312 mmol), palladium (II) acetate (3.5 mg, 0.0158 mmol), triphenylphosphine (12.3 mg, 0.0467 mmol) and sodium carbonate (49.5 mg, 0.467 mmol). The reaction was solvated with DME (0.75 ml) and distilled water (0.25 ml), sealed, and set to stir in a Biotage microwave reactor. The reaction was heated at 150-160° C. for 1 h. At which point the reaction was allowed to cool to room temperature and further diluted with distilled water (10 ml). The aqueous phase was then extracted with DCM (2×20 ml), dried (MgSO$_4$), filtered and the solvent removed in vacuo. The crude residue was subjected to flash column chromatography (eluent petroleum spirit 40-60° C.:EtOAc, 1:1, R$_f$ 0.1). This afforded the title compound as a yellow solid (29.8 mg, 60%).

Examples 13 to 31

The compounds set out below were prepared in the same way as in Example 12, using the appropriate starting materials.

| Example | Compound |
|---|---|
| 13 | [3-(3-Methoxy-phenyl)-thieno[3,2-c]pyridin-4-yl]-thiophen-2-ylmethyl-amine |
| 14 | (3-Phenyl-thieno[3,2-c]pyridin-4-yl)-thiophen-2-ylmethyl-amine |
| 15 | [3-(4-Fluoro-phenyl)-thieno[3,2-c]pyridin-4-yl]thiophen-2-ylmethyl-amine |
| 16 | (3-Benzo[1,3]dioxol-5-yl-thieno[3,2-c]pyridin-4-yl)-thiophen-2-ylmethyl-amine |
| 17 | (2,3-Dihydro-benzo[1,4]dioxin-6-ylmethyl)-[3-(4-fluoro-phenyl)-thieno[3,2-c]pyridin-4-yl]-amine |
| 18 | (2,3-Dihydro-benzo[1,4]dioxin-6-ylmethyl)-(3-phenyl-thieno[3,2-c]pyridin-4-yl)-amine |
| 19 | (2,3-Dihydro-benzo[1,4]dioxin-6-ylmethyl)-[3-(3-methoxy-phenyl)-thieno[3,2-c]pyridin-4-yl]-amine |
| 20 | (3-Benzo[1,3]dioxol-5-yl-thieno[3,2-c]pyridin-4-yl)-(2,3-dihydro-benzo[1,4]dioxin-6-ylmethyl)-amine |
| 21 | Benzyl-(3-phenyl-thieno[3,2-c]pyridin-4-yl)-amine |
| 22 | Benzyl-[3-(4-fluoro-phenyl)-thieno[3,2-c]pyridin-4-yl]-amine |
| 23 | Benzyl-[3-(3-methoxy-phenyl)-thieno[3,2-c]pyridin-4-yl]-amine |
| 24 | Benzyl-(3-p-tolyl-thieno[3,2-c]pyridin-4-yl)-amine |
| 25 | (3-Benzo[1,3]dioxol-5-yl-thieno[3,2-c]pyridin-4-yl)-benzyl-amine |
| 26 | Furan-2-ylmethyl-(3-phenyl-thieno[3,2-c]pyridin-4-yl)amine |
| 27 | [3-(4-Fluoro-phenyl)-thieno[3,2-c]pyridin-4-yl]-furan-2-ylmethyl-amine |
| 28 | Furan-2-ylmethyl-[3-(3-methoxy-phenyl)-thieno[3,2-c]pyridin-4-yl]-amine |
| 29 | Furan-2-ylmethyl-(3-p-tolyl-thieno[3,2-c]pyridin-4-yl)-amine |
| 30 | (4-Phenyl-butyl)-(3-phenyl-thieno[3,2-c]pyridin-4-yl)-amine |
| 31 | (3-Methyl-pyridin-2-ylmethyl)-(3-phenyl-thieno[3,2-c]pyridin-4-yl)-amine |

Example 32

Benzyl-(7-bromo-3-p-tolyl-thieno[3,2-c]pyridin-4-yl)amine

To a solution of benzyl-(3-p-tolyl-thieno[3,2-c]pyridin-4-yl)-amine (314 mg, 0.984 mmol), in THF (5 ml) cooled to 0° C., was added N-bromosuccinimide (168 mg, 0.984 mmol) and the reaction stirred for 1.5 h. The reaction was then allowed to warm to room temperature and the solvent removed in vacuo. The crude residue was partitioned between NH$_4$Cl (25 ml) and DCM (10 ml), the organic layer dried (MgSO$_4$) and the solvent removed in vacuo. No further purification was required. The product was obtained as a yellow solid (390 mg, quantitative).

Example 33

Benzyl-(3,7-di-p-tolyl-thieno[3,2-c]pyridine-4-yl)-amine

A microwave reaction vessel was charged with benzyl-(7-bromo-3-p-tolyl-thieno[3,2-c]pyridin-4-yl)amine (20.0 mg, 0.0489 mmol), 4-methylphenylboronic acid (6.6 mg, 0.0489 mmol), palladium (II) acetate (1.0 mg, 0.00489 mmol), triphenylphosphine (3.8 mg, 0.0147 mmol) and sodium carbonate (15.5 mg, 0.147 mmol). The reaction was solvated in DME (0.75 ml) and distilled water (0.25 ml), the tube sealed, and set to stir in a Biotage microwave reactor. The reaction was heated at 150° C. for 1 h. At which point the reaction was allowed to cool to room temperature and further diluted with distilled water (10 ml). The aqueous phase was then extracted with DCM (2×20 ml), dried (MgSO$_4$), filtered and the solvent removed in vacuo. The crude residue was subjected to flash column chromatography (eluent petroleum spirit 40-60° C.:EtOAc, 10:1, R$_f$ 0.3). This afforded the title compound as a yellow solid (11.0 mg, 53%).

Examples 34 to 45

The compounds set out below were prepared in the same way as in Example 33, using the appropriate starting materials.

| Example | Compound |
|---------|----------|
| 34 | Benzyl-(7-phenyl-3-p-tolyl-thieno[3,2-c]pyridine-4-yl)-amine |
| 35 | 2-(4-Benzylamino-3-p-tolyl-thieno[3,2-c]pyridin-7-yl)-phenol |
| 36 | 3-(4-Benzylamino-3-p-tolyl-thieno[3,2-c]pyridin-7-yl)-phenol |
| 37 | 4-(4-Benzylamino-3-p-tolyl-thieno[3,2-c]pyridin-7-yl)-phenol |
| 38 | 3-(4-Benzylamino-3-p-tolyl-thieno[3,2-c]pyridin-7-yl)-benzoic acid |
| 39 | Benzyl-(7-pyridin-3-yl-3-p-tolyl-thieno[3,2-c]pyridin-4-yl)-amine |
| 40 | Benzyl-(7-pyridin-4-yl-3-p-tolyl-thieno[3,2-c]pyridin-4-yl)-amine |
| 41 | Benzyl-[7-(3-methanesulfonyl-phenyl)-3-p-tolyl-thieno[3,2-c]pyridin-4-yl]-amine |
| 42 | Benzyl-[7-(4-dimethylamino-phenyl)-3-p-tolyl-thieno[3,2-c]pyridin-4-yl]-amine |
| 43 | Benzyl-[7-(2-fluoro-phenyl)-3-p-tolyl-thieno[3,2-c]pyridin-4-yl]-amine |
| 44 | Benzyl-[7-(3-fluoro-phenyl)-3-p-tolyl-thieno[3,2-c]pyridin-4-yl]-amine |
| 45 | Benzyl-[7-(4-fluoro-phenyl)-3-p-tolyl-thieno[3,2-c]pyridin-4-yl]-amine |

Example 46

(E)-2-Methyl-3-(4-phenyl-thiophen-2-yl)-acrylic acid

A 50 ml round bottomed flask was charged with diethylphosphite (684 µl, 5.31 mmol) and treated sequentially with sodium hydride (637 mg, 15.94 mmol, 60% in mineral oil) in DME (20 ml), followed by 2-bromopropionic acid (478 µl, 5.31 mmol). The reaction was stirred at room temperature until hydrogen evolution ceased. Next 4-phenyl-2-thiophenecarboxaldehyde (1.0 g, 5.31 mmol) was added and the reaction stirred for 1 h. The reaction was quenched by the addition of EtOH (5 ml) and the contents of the flask poured into distilled water (20 ml). The strongly basic solution was washed with diethyl ether (25 ml) to remove traces of mineral oil, the aqueous layer acidified to pH 4 with concentrated HCl and extracted with diethyl ether (2×25 ml). The organic layer was dried (MgSO$_4$) and the solvent removed in vacuo. The crude residue was washed with petroleum spirit 40-60° C., and the resulting insoluble solid, fractionally crystallized from dichloromethane to afford the title compound as a white solid (335.2 mg, 29%).

Example 47

2-Methyl-3-(4-phenyl-thiophen-2-yl)-acryloyl azide

To a solution of (E)-2-methyl-3-(4-phenyl-thiophen-2-yl)-acrylic acid (924 mg, 3.78 mmol) and triethylamine (617 µl, 4.43 mmol) in THF (10 ml) was added diphenylphosphoryl azide (897 µl, 6.27 mmol) at 0° C. The reaction was next stirred for 4 h at room temperature. At which point the contents of the reaction flask were partitioned between ethyl acetate (25 ml) and sodium hydrogencarbonate (25 ml). The organic phase was separated and the solvent removed in vacuo. The crude residue was suspended between methanol (25 ml) and distilled water (25 ml), the precipitate collected and dried (MgSO$_4$) to afford the title compound as a white solid.

Example 48

6-Methyl-3-phenyl-5H-thieno[3,2-c]pyridin-4-one

2-Methyl-3-(4-phenyl-thiophen-2-yl)-acryloyl azide, was dissolved in toluene (20 ml) and heated at 120° C. for 0.5 h. The solvent was then removed in vacuo and the residue dissolved in 1,2-dichlorobenzene (20 ml), to which was added a few flakes of iodine. The reaction was next heated to 170° C. and this was maintained for 2 h. The reaction was then allowed to cool to room temperature and the solvent removed in vacuo. Ethanol (25 ml) was added to the reaction flask and the precipitate formed, collected and filtered to afford the title compound to as a white solid which required no further purification (362 mg, 65% over 2 steps from (E)-2-methyl-3-(4-phenyl-thiophen-2-yl)-acrylic acid).

Example 49

4-Chloro-6-methyl-3-phenyl-thieno[3,2-c]pyridine

6-Methyl-3-phenyl-5H-thieno[3,2-c]pyridin-4-one (362 mg, 1.5 mmol) and POCl$_3$ (15 ml) was stirred for 3 h at 120° C. After evaporation of POCl$_3$, the crude residue was partitioned between dichloromethane (25 ml) and sodium hydrogencarbonate (25 ml). The organic phase was dried (MgSO$_4$) and the solvent removed in vacuo to afford the title compound as a yellow oil (254 mg, 65%) which required no further purification.

Example 50

Benzyl-(6-methyl-3-phenyl-thieno[3,2-c]pyridin-4-yl)-amine

A microwave reaction vessel was charged with 4-chloro-6-methyl-3-phenyl-thieno[3,2-c]pyridine (254 mg, 0.982 mmol), benzylamine (642 µl, 5.886 mmol), triethylamine (137 µl, 0.982), solvated in NMP (3 ml), and set to stir in a Biotage microwave reactor. The reaction was heated at 220° C. for 6 h. The crude reaction was next partitioned between ethyl acetate (25 ml) and distilled water (25 ml). The organic phase was dried (MgSO$_4$) and the solvent removed in vacuo. Purification by flash column chromatography (petroleum spirit 40-60° C.:ethyl acetate, 5:1, R$_f$ 0.5) afforded the title compound as a yellow solid (200.4 mg, 62%).

Example 51

Analytical data for compounds representative of the above examples are shown in the table below.

| Example | Compound Name | Mass Spectrum (m/z) |
|---|---|---|
| 4 | 3-Bromo-4-chloro-thieno[3,2-c]pyridine | 7.06 min, 250 (ES+, 100%, [M + H]) |
| 5 | (3-Bromo-thieno[3,2-c]pyridin-4-yl)-pyridin-2-ylmethyl-amine | 6.92 min, 322 (ES+, 100%, [M + H]) |
| 6 | (3-Bromo-thieno[3,2-c]pyridin-4-yl)-(2,3-dihydro-benzo[1,4]dioxin-6-ylmethyl)-amine | 7.47 min, 377 (ES+, 100%, [M + H]) |
| 7 | Benzyl-(3-bromo-thieno[3,2-c]pyridin-4-yl)-amine | 8.21 min, 321 (ES+, 100%, [M + H]) |
| 8 | (3-Bromo-thieno[3,2-c]pyridin-4-yl)-thiophen-2-ylmethyl-amine | 7.64 min, 327 (ES+, 100%, [M + H]) |
| 9 | (3-Bromo-thieno[3,2-c]pyridin-4-yl)-furan-2-ylmethyl-amine | 7.63 min, 309 (ES+, 100%, [M + H]) |
| 10 | (3-Bromo-thieno[3,2-c]pyridin-4-yl)-(4-phenyl-butyl)-amine | 9.08 min, 361 (ES+, 100%, [M + H]) |
| 11 | (3-Bromo-thieno[3,2-c]pyridin-4-yl)-(3-methyl-pyridin-2-ylmethyl)-amine | 8.12 min, 334 (ES+, 100%, [M + H]) |
| 12 | (3-Phenyl-thieno[3,2-c]pyridin-4-yl)-pyridin-2ylmethyl-amine | 7.29 min, 318 (ES+, 100%, [M + H]) |
| 13 | [3-(3-Methoxy-phenyl)-thieno[3,2-c]pyridin-4-yl]-thiophen-2-ylmethyl-amine | 8.08 min, 353 (ES+, 100%, [M + H]) |
| 14 | (3-Phenyl-thieno[3,2-c]pyridin-4-yl)-thiophen-2-ylmethyl-amine | 8.21 min, 323 (ES+, 100%, [M + H]) |
| 15 | [3-(4-Fluoro-phenyl)-thieno[3,2-c]pyridin-4-yl]thiophen-2-ylmethyl-amine | 8.08 min, 341 (ES+, 100%, [M + H]) |
| 16 | (3-Benzo[1,3]dioxol-5-yl-thieno[3,2-c]pyridin-4-yl)-thiophen-2-ylmethyl-amine | 7.86 min, 367 (ES+, 100%, [M + H]) |
| 17 | (2,3-Dihydro-benzo[1,4]dioxin-6-ylmethyl)-[3-(4-fluoro-phenyl)-thieno[3,2-c]pyridin-4-yl]-amine | 7.99 min, 393 (ES+, 100%, [M + H]) |
| 18 | (2,3-Dihydro-benzo[1,4]dioxin-6-ylmethyl)-(3-phenyl-thieno[3,2-c]pyridin-4-yl)-amine | 7.64 min, 375 (ES+, 100%, [M + H]) |
| 19 | (2,3-Dihydro-benzo[1,4]dioxin-6-ylmethyl)-[3-(3-methoxy-phenyl)-thieno[3,2-c]pyridin-4-yl]-amine | 8.00 min, 405 (ES+, 100%, [M + H]) |
| 20 | (3-Benzo[1,3]dioxol-5-yl-thieno[3,2-c]pyridin-4-yl)-(2,3-dihydro-benzo[1,4]dioxin-6-ylmethyl)-amine | 7.71 min, 419 (ES+, 100%, [M + H]) |
| 21 | Benzyl-(3-phenyl-thieno[3,2-c]pyridin-4-yl)-amine | 8.34 min, 317 (ES+, 100%, [M + H]) |
| 22 | Benzyl-[3-(4-fluoro-phenyl)-thieno[3,2-c]pyridin-4-yl]-amine | 8.25 min, 335 (ES+, 100%, [M + H]) |
| 23 | Benzyl-[3-(3-methoxy-phenyl)-thieno[3,2-c]pyridin-4-yl]-amine | 8.38 min, 347 (ES+, 100%, [M + H]) |
| 24 | Benzyl-(3-p-tolyl-thieno[3,2-c]pyridin-4-yl)-amine | 8.74 min, 331 (ES+, 100%, [M + H]) |
| 25 | (3-Benzo[1,3]dioxol-5-yl-thieno[3,2-c]pyridin-4-yl)-benzyl-amine | 8.02 min, 361 (ES+, 100%, [M + H]) |
| 26 | Furan-2-ylmethyl-(3-phenyl-thieno[3,2-c]pyridin-4-yl)amine | 7.96 min, 307 (ES+, 100%, [M + H]) |
| 27 | [3-(4-Fluoro-phenyl)-thieno[3,2-c]pyridin-4-yl]-furan-2-ylmethyl-amine | 7.91 min, 325 (ES+, 100%, [M + H]) |
| 28 | Furan-2-ylmethyl-[3-(3-methoxy-phenyl)-thieno[3,2-c]pyridin-4-yl]-amine | 7.91 min, 337 (ES+, 100%, [M + H]) |
| 29 | Furan-2-ylmethyl-(3-p-tolyl-thieno[3,2-c]pyridin-4-yl)-amine | 8.31 min, 321 (ES+, 100%, [M + H]) |
| 30 | (3-Benzo[1,3]dioxol-5-yl-thieno[3,2-c]pyridin-4-yl)-furan-2-ylmethyl-amine | 7.72 min, 351 (ES+, 100%, [M + H]) |
| 31 | (4-Phenyl-butyl)-(3-phenyl-thieno[3,2-c]pyridin-4-yl)-amine | 8.93 min, 359 (ES+, 100%, [M + H]) |
| 32 | (3-Methyl-pyridin-2-ylmethyl)-(3-phenyl-thieno[3,2-c]pyridin-4-yl)-amine | 8.31 min, 332 (ES+, 100%, [M + H]) |
| 33 | Benzyl-(3,7-di-p-tolyl-thieno[3,2-c]pyridine-4-yl)-amine | 10.56 min, 421 (ES+, 100%, [M + H]) |
| 34 | Benzyl-(7-phenyl-3-p-tolyl-thieno[3,2-c]pyridine-4-yl)-amine | 9.98 min, 407 (ES+, 100%, [M + H]) |
| 35 | 2-(4-Benzylamino-3-p-tolyl-thieno[3,2-c]pyridin-7-yl)-phenol | 8.31 min, 423 (ES+, 100%, [M + H]) |
| 36 | 3-(4-Benzylamino-3-p-tolyl-thieno[3,2-c]pyridin-7-yl)-phenol | 8.34 min, 423 (ES+, 100%, [M + H]) |
| 37 | 4-(4-Benzylamino-3-p-tolyl-thieno[3,2-c]pyridin-7-yl)-phenol | 8.24 min, 423 (ES+, 100%, [M + H]) |
| 38 | 3-(4-Benzylamino-3-p-tolyl-thieno[3,2-c]pyridin-7-yl)-benzoic acid | 6.58 min, 451 (ES+, 100%, [M + H]) |
| 39 | Benzyl-(7-pyridin-3-yl-3-p-tolyl-thieno[3,2-c]pyridin-4-yl)-amine | 8.58 min, 408 (ES+, 100%, [M + H]) |
| 40 | Benzyl-(7-pyridin-4-yl-3-p-tolyl-thieno[3,2-c]pyridin-4-yl)-amine | 8.78 min, 408 (ES+, 100%, [M + H]) |
| 41 | Benzyl-[7-(3-methanesulfonyl-phenyl)-3-p-tolyl-thieno[3,2-c]pyridin-4-yl]-amine | 8.33 min, 485 (ES+, 100%, [M + H]) |

-continued

| Example | Compound Name | Mass Spectrum (m/z) |
|---|---|---|
| 42 | Benzyl-[7-(4-dimethylamino-phenyl)-3-p-tolyl-thieno[3,2-c]pyridin-4-yl]-amine | 9.98 min, 450 (ES+, 100%, [M + H]) |
| 43 | Benzyl-[7-(2-fluoro-phenyl)-3-p-tolyl-thieno[3,2-c]pyridin-4-yl]-amine | 9.42 min, 425 (ES+, 100%, [M + H]) |
| 44 | Benzyl-[7-(3-fluoro-phenyl)-3-p-tolyl-thieno[3,2-c]pyridin-4-yl]-amine | 9.97 min, 425 (ES+, 100%, [M + H]) |
| 45 | Benzyl-[7-(4-fluoro-phenyl)-3-p-tolyl-thieno[3,2-c]pyridin-4-yl]-amine | 9.98 min, 425 (ES+, 100%, [M + H]) |
| 46 | (E)-2-Methyl-3-(4-phenyl-thiophen-2-yl)-acrylic acid | 6.36 min, 245 (ES+, 100%, [M + H]) |
| 48 | 6-Methyl-3-phenyl-5H-thieno[3,2-c]pyridin-4-one | 6.49 min, 242 (ES+, 100%, [M + H]) |
| 49 | 4-Chloro-6-methyl-3-phenyl-thieno[3,2-c]pyridine | 7.88 min, 260 (ES+, 100%, [M + H]) |
| 50 | Benzyl-(6-methyl-3-phenyl-thieno[3,2-c]pyridin-4-yl)-amine | 9.30 min, 331 (ES+, 100%, [M + H]) |

Example 52

Kv1.3 Autopatch Electrophysiology Method

Cells stably transfected with cDNA for human Kv1.3 (in pcDNA3.1) were grown in Ex-cell 302 serum-free medium for CHO cells, supplemented with 10 μl/ml [100×] glutamine, 500 μg/ml G418 (gentimicin), and 1% HT supplement (50×, hypoxanthine and thymidine). Compounds were tested on these cells using the AutoPatch technology in whole cell mode.

The external bathing solution contained (in mM): 150 NaCl, 10 KCl, 1 $MgCl_2$, 3 $CaCl_2$, 10 HEPES, pH 7.4 with NaOH. Patch pipettes were filled with an electrode solution of composition (in mM): 100 K-Gluconate, 20 KCl, 1 $MgCl_2$, 1 $CaCl_2$, 10 HEPES, 11 EGTA, 5 ATP—$Na_2$, 2 Glutathione pH 7.2 with KOH.

Compounds were dissolved in DMSO (100%) and made up in the external bather at a concentration of 1 μM. All experiments were conducted at room temperature (22-24° C.).

A cell suspension (10 ml), with a density of 100,000 cells/ml, was aliquoted into a 15 ml centrifuge tube and transferred to an incubator (37° C., 5% $CO_2$) for approximately one hour before use. Following 60 min incubation, a tube was taken and centrifuged at 1000 rpm for 4 mins at room temperature. 9.5 ml supernatant was thence discarded, leaving a cell pellet at the bottom of the tube. The pellet was then resuspended using 100 μl of cold (4° C.), filtered (0.22 μm), 0.2% BSA/bather solution (0.02 g BSA/10 ml bather). The bottom of the tube was manually agitated gently until the solution became cloudy with cells. The 100 μl cell resuspension solution was then stored on the bench at 4° C. (using a Peltier-based temperature control device) until used.

A length of capillary glass (1B150F-4, WPI) was dipped into the cell suspension solution, such that ~3 cm column of fluid was taken up by capillary action. A Ag/AgCl wire was dropped into the non-dipped end of the capillary also. The outside of the solution-filled end of the capillary was then dried and the capillary was loaded into the AutoPatch™. Borosilicate glass patch pipettes (from 1.5 mm OD, thin-walled filamented, GC150-TF capillary glass, Harvard) were pulled using a DMZ pipette puller (Zeitz Instruments), and were back-filled using the internal pipette solution, being careful that no bubbles remain at the tip or in the body of the pipette. Patch pipettes typically had resistances of 2.3-3.5 MΩ. Once filled, the pipette tip and a proportion of the shaft (~15 mm) were dipped into Sigmacote (Sigma). The recording pipette was then loaded into the AutoPatch™. Automated patch-clamping was initiated by the operator, but thereafter AutoPatch.exe continued the experiment providing that preset conditions and criteria were satisfied.

Whole cell patch-clamp recordings were made using the AutoPatch™ rig, which incorporated an EPC9 or EPC10 amplifier (HEKA, Germany) under control of Pulse software (v8.54 or v8.76, HEKA, Germany), a motion controller with 2 translators (Newport, UK), valve controller (VF1) and a c-level suction device all at room temperature (22-24° C.). This equipment was completely under the control of AutoPatch.exe and operator intervention was only made when there was a requirement to refill the drug reservoirs or to prevent the loss of a cell due to a technical error. Cells with an $R_{series}$ greater than 18 MΩ were discounted from the experiment.

Qualification stages prior to perfusion and drug application ensured that the observed current met the criteria for the experiment. Only those cells with an $I_K$>400 pA were used for experiments. Cells were continuously perfused with external solution at a flow rate of 1.8-2 ml/minute. The perfusion chamber had a working volume of 80-85 μl and allowed for rapid exchange of drug solutions. Online analysis of the $hK_v1.3$ current during the application of compounds was performed by the AutoPatch™ software. Voltage-step protocols and analysis of data was performed as described for conventional electrophysiology.

Electrophysiology voltage-step protocols and analysis of data was performed as follows. Data was sampled at 5 kHz, and filtered with a −3 dB bandwidth of 2.5 kHz. Cells were held at a voltage of −80 mV. Currents were evoked by a voltage step to +30 mV for 500 ms in duration every 10 s. Currents were analysed using Pulsefit software (v8.54 or v8.76, HEKA, Germany), with the total charge measured during the whole of voltage step. All other plots were produced using Igor Pro (WaveMetrics).

Example 53

Kv1.5 Autopatch Electrophysiology Method

Cells stably transfected with cDNA for human Kv1.5 (in pEF6::VA-His-TOPO) were grown in Ex-cell 302 serum-free medium for CHO cells, supplemented with 10 μl/ml [100×] glutamine, 5 μg/ml blasticidin and 1% HT supplement (50×, hypoxanthine and thymidine). Compounds were tested on these cells using the AutoPatch technology in whole cell mode.

The external bathing solution contained (in mM): 150 NaCl, 10 KCl, 1 MgCl$_2$, 3 CaCl$_2$, 10 HEPES, pH 7.4 with NaOH. Patch pipettes were filled with an electrode solution of composition (in mM): 160 KCl, 0.5 MgCl$_2$, 10 HEPES, 1 EGTA, pH 7.4 with KOH.

Compounds were dissolved in DMSO (100%) and made up in the external bather at a concentration of 1 µM. All experiments were conducted at room temperature (22-24° C.).

A cell suspension (10 ml), with a density of 100,000 cells/ml, was aliquoted into a 15 ml centrifuge tube and transferred to an incubator (37° C., 5% CO$_2$) for approximately one hour before use. Following 60 min incubation, a tube was taken and centrifuged at 1000 rpm for 4 mins at room temperature. 9.5 ml supernatant was thence discarded, leaving a cell pellet at the bottom of the tube. The pellet was then resuspended using 100 µl of cold (4° C.), filtered (0.22 µm), 0.2% BSA/bather solution (0.02 g BSA/10 ml bather). The bottom of the tube was manually agitated gently until the solution became cloudy with cells. The 100 µl cell resuspension solution was then stored on the bench at 4° C. (using a Peltier-based temperature control device) until used.

A length of capillary glass (1B150F-4, WPI) was dipped into the cell suspension solution, such that ~3 cm column of fluid was taken up by capillary action. A Ag/AgCl wire was dropped into the non-dipped end of the capillary also. The outside of the solution-filled end of the capillary was then dried and the capillary was loaded into the AutoPatch™. Borosilicate glass patch pipettes (from 1.5 mm OD, thin-walled filamented, GC150-TF capillary glass, Harvard) were pulled using a DMZ pipette puller (Zeitz Instruments), and were back-filled using the internal pipette solution, being careful that no bubbles remain at the tip or in the body of the pipette. Patch pipettes typically had resistances of 2.3-3.5 MΩ. Once filled, the pipette tip and a proportion of the shaft (~15 mm) were dipped into Sigmacote (Sigma). The recording pipette was then loaded into the AutoPatch™. Automated patch-clamping was initiated by the operator, but thereafter AutoPatch.exe continued the experiment providing that preset conditions and criteria were satisfied.

Whole cell patch-clamp recordings were made using the AutoPatch™ rig, which incorporated an EPC9 or EPC10 amplifier (HEKA, Germany) under control of Pulse software (v8.54 or v8.76, HEKA, Germany), a motion controller with 2 translators (Newport, UK), valve controller (VF1) and a c-level suction device all at room temperature (22-24° C.). This equipment was completely under the control of AutoPatch.exe and operator intervention was only made when there was a requirement to refill the drug reservoirs or to prevent the loss of a cell due to a technical error. Cells with an R$_{series}$ greater than 18 MΩ were discounted from the experiment.

Qualification stages prior to perfusion and drug application ensured that the observed current met the criteria for the experiment. Only those cells with an I$_K$>500 pA were used for experiments. Cells were continuously perfused with external solution at a flow rate of 1.8-2 ml/minute. The perfusion chamber had a working volume of 80-85 µl and allowed for rapid exchange of drug solutions. Online analysis of the hK$_v$1.5 current during the application of compounds was performed by the AutoPatch™ software. Voltage-step protocols and analysis of data was performed as described for conventional electrophysiology.

Electrophysiology voltage-step protocols and analysis of data was performed as follows. Data was sampled at 5 kHz and filtered with a -3 dB bandwidth of 2.5 kHz. Cells were held at a voltage of -80 mV. Currents were evoked by a voltage step to 0 mV for 1000 ms in duration followed by a step to -40 mV for 1000 ms every 5 s. Currents were analysed using Pulsefit software (v8.54 or v8.76, HEKA, Germany), with the total charge measured during 75-95% of the 0 mV voltage step. All other plots were produced using Igor Pro (WaveMetrics).

Example 54

Representative Activity Data is Provided in the Table Below

| Example | Kv 1.3% Inhibition at 1 µM | Kv 1.5% Inhibition at 1 µM |
| --- | --- | --- |
| 12 | 46.1 | 59.6 |
| 13 | 83.2 | 89.4 |
| 14 | 91.2 | 81.9 |
| 15 | 91.9 | 87.2 |
| 16 | 90.3 | 81.2 |
| 17 | 59.6 | 86.1 |
| 18 | 76.9 | 85.3 |
| 19 | 73.5 | 75.6 |
| 20 | 83.5 | 90.2 |
| 21 | 61.5 | 77.4 |
| 22 | 68.6 | 90.2 |
| 23 | 58.0 | 79.6 |
| 24 | 81.2 | 90.2 |
| 25 | 58.1 | 70.5 |
| 26 | 48.4 | 80.4 |
| 27 | 45.9 | 70.4 |
| 28 | 72.7 | 91.9 |
| 29 | 66.2 | 86.1 |
| 30 | 82.8 | 65.8 |
| 31 | 71.8 | 78.4 |
| 33 | 24.4 | 39.2 |
| 34 | 8.1 | 25.6 |
| 35 | 12.6 | 33.3 |
| 36 | 15.5 | 52.4 |
| 37 | 15.7 | 39.9 |
| 38 | 41.3 | 84.8 |
| 39 | 50.1 | 90.0 |
| 40 | 49.9 | 36.3 |
| 41 | 26.3 | 39.8 |
| 42 | 24.1 | 14.5 |
| 43 | 13.6 | 26.3 |
| 44 | 29.6 | 18.8 |
| 45 | 34.0 | 24.7 |
| 50 | 23.7 | 50.8 |

ABBREVIATIONS

CHO Chinese Hamster Ovary Cells
DCM Dichloromethane
DMEM Dulbecco's Modified Eagle media
DME 1,2-Dimethoxyethane
EAE Experimental autoimmune encephalomyelitis
EBSS Earls Balanced Salt Solution
EtOAc Ethyl acetate
EtOH Ethanol
FCS Fetal Calf Serum
GLUT4 Insulin-regulated glucose transporter
HCl Hydrochloric acid
HT Hydroxytryptamine
Kv$_{(ur)}$ Cardiac Ultrarapid Delayed Rectifier
NMP N-Methylpyrrolidinone
Na$_2$SO$_4$ Sodium sulfate
Ammonium chloride
NH$_4$Cl Magnesium sulfate
MS Multiple sclerosis
POCl$_3$ Phosphorous oxychloride $T_{CM}$ Central memory T cell
$T_{EM}$ Effector memory T cell
THF Tetrahydrofuran
WCPC Whole-Cell Patch-Clamp It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

REFERENCES

Brendel and Peukert 'Blockers of the Kv1.5 Channel for the Treatment of Atrial Arrhythmias', Expert Opinion in Therapeutic Patents, 12 (11), 1589-1598 (2002).

Feng et al., "Effects of class III antiarrhythmic drugs on transient outward and ultra-rapid delayed rectifier currents in human atrial myocytes", J Pharmacol Exp Ther, 281(1), 384-392, 1997.

Wang et al., "Effects of flecainide, quinidine, and 4-aminopyridine on transient outward and ultrarapid delayed rectifier currents in human atrial myocytes", J Pharmacol, 272(1), 184-196, 1995.

Malayev et al., "Mechanism of clofilium block of the human Kv1.5 delayed rectifier potassium channel", Mol Pharmaco, 147(1), 198-205, 1995.

Godreau et al., "Mechanisms of action of antiarrhythmic agent bertosamil on hKv1.5 channels and outward potassium current in human atrial myocytes", J Pharmacol Exp Ther 300(2), 612-620, 2002.

Peukert S, et al., Identification, synthesis, and activity of novel blockers of the voltage-gated potassium channel Kv1.5. J Med Chem. February 13; 46(4):486-98, 2003.

Xu & Xu, "The expression of arrhythmic related genes on *Xenopus oocytes* for evaluation of class III antiarrhythmic drugs from ocean active material", Yi Chuan Xue Bao, 27 (3), 195-201, 2000.

Desir G V, "Kv1.3 Potassium Channel Blockade as an Approach to Insulin Resistance", Expert Opin. Ther. Targets, 9 (3), 571-579, 2005.

Lan M et al., "Expression of Delayed Rectifier Potassium Channels and their Possible Roles in Proliferation of Human Gastric Cancer Cells", Cancer Biology & Therapy, 12(4), 1342-1347, 2005.

Liang C-Z et al., "K+ Channel Expression in Prostate Epithelium and its Implications in Men with Chronic Prostatitis", BJU International, 97, 190-192, 2006.

Erdogan A et al., "Maratoxin Inhibits VEGF-Induced Hyperpolarization,
Proliferation and Nitric Oxide Production of Human Endothelial Cells", J Vasc Res., 42, 368-376, 2005.

Wulff H et al., "The Voltage-gated Kv1.3 K+ Channel in Effector Memory T Cells as New Targets for MS", J. Clin. Invest., 111, 1703-1713, 2003

Wulff H et al., "K+ Channel Expression During B Cell Differentiation: Implications for Immunomodulation and Autoimmunity", J Immunol., 173, 776-786, 2004.

Nguyen A et al., "Novel Nonpeptide Agents Potently Block the C-Type Inactivated Conformation of Kv1.3 and Suppress T Cell Activation", Mol. Pharmacol., 50, 1672-1679, 1996.

Hanson D C et al., "UK-78,282, a Novel Piperidine Compound That Potently Blocks the Kv1.3 Voltage-Gated Potassium Channel and Inhibits Human T Cell Activation", Br. J. Pharmacol., 126, 1707-1716, 1999.

Felix J P et al., "Identification and Biochemical Characterization of a Novel Norterpene Inhibitor of the Human Lymphocyte Voltage-Gated Potassium Channel, Kv1.3", Biochemistry, 38 (16), 4922-4930, 1999.

Baell J B et al., "Khellinone Derivatives as Blockers of he Voltage-Gated Potassium Channel Kv1.3: Synthesis and Immunosuppressive Activity" J. Med. Chem., 47, 2326-2336, 2004.

Schmitz A et al., "Design of PAP-1, a Selective Small Molecule Kv1.3 Blocker, for the Suppression of Effector Memory T Cells in Autoimmune Diseases", Mol. Pharmacol., 15669, 2005.

Eloy F et al, Helv. Cjim. Acta; 53, 645-67, 1970.

Bisagni E et al, Bull. Soc. Chim. France, 515-518, 1974.

Having now fully described this invention, it will be understood by those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound of the formula:

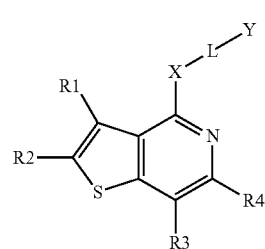

wherein:

R1 is unsubstituted or substituted aryl, wherein the substituents are selected from the group consisting of cyano, halogen, nitro, trifluoromethyl, unsubstituted alkyl, alkylthio, alkoxy, NR9R10, $CO_2R7$, C(O)NR9R10, NHC(O)R7, $SO_2NR9R10$, and hydroxyl; or unsubstituted or substituted heteroaryl, wherein the substituents are selected from the group consisting of cyano, nitro, halogen, unsubstituted alkyl, alkylthio, alkoxy, NR9R10, $CO_2R7$, C(O)NR9R10, NHC(O)R7, $SO_2NR9R10$ and hydroxyl;

R2 is H or unsubstituted or substituted alkyl, wherein the substituents are selected from the group consisting of halogen, cyano, nitro, NR9R10, alkoxy, hydroxyl, unsubstituted aryl, unsubstituted heteroaryl, aryloxy, heteroaryloxy, $CO_2R7$, C(O)NR9R10, NHC(O)R7 and $SO_2NR9R10$;

R3 is unsubstituted or substituted alkyl, wherein the substituents are selected from the group consisting of halogen, cyano, nitro, NR9R10, alkoxy, hydroxyl, unsubstituted aryl, unsubstituted heteroaryl, aryloxy, heteroaryloxy, $CO_2R7$, C(O)NR9R10, NHC(O)R7 and $SO_2NR9R10$; unsubstituted alkoxy; unsubstituted or substituted aryl, wherein the substituents are selected from the group consisting of cyano, halogen, nitro, trifluoromethyl, unsubstituted alkyl, alkylthio, alkoxy, NR9R10, $CO_2R7$, C(O)NR9R10, NHC(O)R7, $SO_2NR9R10$, and hydroxyl; or NR5R6;

R4 is H; unsubstituted or substituted alkyl, wherein the substituents are selected from the group consisting of halogen, cyano, nitro, NR9R10, alkoxy, hydroxyl, unsubstituted aryl, unsubstituted heteroaryl, aryloxy, heteroaryloxy, $CO_2R7$, $C(O)NR9R10$, $NHC(O)R7$ and $SO_2NR9R10$; unsubstituted alkoxy; unsubstituted or substituted aryl, wherein the substituents are selected from the group consisting of cyano, halogen, nitro, trifluoromethyl, unsubstituted alkyl, alkylthio, alkoxy, $NR9R10$, $CO_2R7$, $C(O)NR9R10$, $NHC(O)R7$, $SO_2NR9R10$, and hydroxyl; or $NR5R6$;

R5 and R6 may be the same or different, and may be H; unsubstituted or substituted alkyl, wherein the substituents are selected from the group consisting of halogen, cyano, nitro, alkoxy, hydroxyl, unsubstituted aryl, unsubstituted heteroaryl, aryloxy, and heteroaryloxy; unsubstituted or substituted aryl, wherein the substituents are selected from the group consisting of cyano, halogen, nitro, trifluoromethyl, unsubstituted alkyl, alkylthio, alkoxy, $NR9R10$, $CO_2R7$, $C(O)NR9R10$, $NHC(O)R7$, $SO_2NR9R10$, and hydroxyl; unsubstituted or substituted heteroaryl, wherein the substituents are selected from the group consisting of cyano, nitro, halogen, unsubstituted alkyl, alkylthio, alkoxy, $NR9R10$, $CO_2R7$, $C(O)NR9R10$, $NHC(O)R7$, $SO_2NR9R10$ and hydroxyl; or unsubstituted cycloalkyl; or R5 and R6 may together form a saturated or partially saturated 4 to 7 membered ring, wherein said ring may optionally comprise one or more further heteroatoms selected from N, O or S;

R7 is H; unsubstituted or substituted alkyl, wherein the substituents are selected from the group consisting of halogen, cyano, nitro, alkoxy, hydroxyl, unsubstituted aryl, unsubstituted heteroaryl, aryloxy, and heteroaryloxy; unsubstituted or substituted aryl, wherein the substituents are selected from the group consisting of cyano, halogen, nitro, trifluoromethyl, unsubstituted alkyl, alkylthio, and alkoxy; unsubstituted or substituted heteroaryl, wherein the substituents are selected from the group consisting of cyano, nitro, halogen, unsubstituted alkyl, alkylthio, and alkoxy; or unsubstituted cycloalkyl;

X is NR8;

R8 is H;

L is $(CH_2)_n$, where n is 0, 1, 2, 3 or 4;

Y is unsubstituted or substituted aryl, wherein the substituents are selected from the group consisting of cyano, halogen, nitro, trifluoromethyl, unsubstituted alkyl, alkylthio, alkoxy, $NR9R10$, $CO_2R7$, $C(O)NR9R10$, $NHC(O)R7$, $SO_2NR9R10$, and hydroxyl; or unsubstituted or substituted heteroaryl, wherein the substituents are selected from the group consisting of cyano, nitro, halogen, unsubstituted alkyl, alkylthio, alkoxy, $NR9R10$, $CO_2R7$, $C(O)NR9R10$, $NHC(O)R7$, $SO_2NR9R10$ and hydroxyl; and R9 and R10 can be the same or different, and may be H, unsubstituted alkyl, unsubstituted aryl, unsubstituted heteroaryl, unsubstituted cycloalkyl, aminoethyl, methylaminoethyl, dimethylaminoethyl, hydroxyethyl, or alkoxyethyl, or R9 and R10 may together form a saturated or partially saturated 4 to 7 membered ring; or the products of oxidation of sulphur and/or nitrogen moieties on these molecules, or a pharmaceutically acceptable salt thereof.

2. A compound which is:
Benzyl-(3,7-di-p-tolyl-thieno[3,2-c]pyridine-4-yl)-amine;
Benzyl-(7-phenyl-3-p-tolyl-thieno[3,2-c]pyridine-4-yl)-amine;
2-(4-Benzylamino-3-p-tolyl-thieno[3,2-c]pyridin-7-yl)-phenol;
3-(4-Benzylamino-3-p-tolyl-thieno[3,2-c]pyridin-7-yl)-phenol;
4-(4-Benzylamino-3-p-tolyl-thieno[3,2-c]pyridin-7-yl)-phenol;
3-(4-Benzylamino-3-p-tolyl-thieno[3,2-c]pyridin-7-yl)-benzoic acid;
Benzyl-(7-pyridin-3-yl-3-p-tolyl-thieno[3,2-c]pyridin-4-yl)-amine;
Benzyl-(7-pyridin-4-yl-3-p-tolyl-thieno[3,2-c]pyridin-4-yl)-amine;
Benzyl-[7-(3-methanesulfonyl-phenyl)-3-p-tolyl-thieno[3,2-c]pyridin-4-yl]-amine;
Benzyl-[7-(4-dimethylamino-phenyl)-3-p-tolyl-thieno[3,2-c]pyridin-4-yl)-amine;
Benzyl-[7-(2-fluoro-phenyl)-3-p-tolyl-thieno[3,2-c]pyridin-4-yl]-amine;
Benzyl-[7-(3-fluoro-phenyl)-3-p-tolyl-thieno[3,2-c]pyridin-4-yl]-amine; or
Benzyl-(7-(4-fluoro-phenyl)-3-p-tolyl-thieno[3,2-c]pyridin-4-yl]-amine;
or pharmaceutically acceptable salts thereof.

3. A compound as claimed in claim 1, wherein the thieno[3,2c]pyridine moiety has been oxidized to:
Thieno[3,2c]pyridine-1-oxide;
Thieno[3,2c]pyridine-1,1-dioxide;
Thieno[3,2c]pyridine-1,1,5,-trioxide;
Thieno[3,2c]pyridine-1,5,-dioxide; or
Thieno[3,2c]pyridine-5-oxide.

4. A pharmaceutical composition comprising at least one compound as claimed in claims 1 or 2 optionally together with one or more pharmaceutically acceptable excipients, diluents and/or carriers.

5. A method for the treatment of type 2 diabetes or arrhythmia, comprising administering to a subject an effective amount of at least one compound as defined in claims 1 or 2.

6. A method for the treatment of type 2 diabetes or arrhythmia, comprising administering to a subject a pharmaceutical composition comprising at least one compound as claimed in claims 2 or 4 optionally together with one or more pharmaceutically acceptable excipients, diluents and/or carriers.

7. A method as claimed in claim 6 wherein the disorder is type 2 diabetes.

8. A method as claimed in claim 6 wherein the disorder is arrhythmia.

9. A pharmaceutical composition comprising a compound of claim 3 optionally together with one or more pharmaceutically acceptable excipients, diluents and/or carriers.

10. The compound as claimed in claim 1 wherein:
R7 is H or unsubstituted alkyl; and
Y is unsubstituted or substituted aryl, wherein the substituents are selected from the group consisting of cyano, halogen, nitro, trifluoromethyl, unsubstituted alkyl, alkylthio, alkoxy, $NR9R10$, $CO_2R7$, $C(O)NR9R10$, $NHC(O)R7$, $SO_2NR9R10$, and hydroxyl; or unsubstituted or substituted heteroaryl wherein the substituents are selected from the group consisting of cyano, nitro, halogen, unsubstituted alkyl, alkylthio, alkoxy, $NR9R10$, $CO_2R7$, $C(O)NR9R10$, $NHC(O)R7$, $SO_2NR9R10$ and hydroxyl.

11. The compound as claimed in claim 1, wherein the sulphur and/or nitrogen moieties on these molecules are not oxidized, or a pharmaceutically acceptable salt thereof.

* * * * *